US006531449B2

(12) United States Patent
Khojasteh et al.

(10) Patent No.: US 6,531,449 B2
(45) Date of Patent: Mar. 11, 2003

(54) HEXAHYDROPYRAZOLO[4,3,-C]PYRIDINE METABOLITES

(75) Inventors: S. Cyrus Khojasteh, Berkeley, CA (US); John P. O'Donnell, N. Stonington, CT (US)

(73) Assignee: Pfizer Inc., New York, NY (US)

( * ) Notice: Subject to any disclaimer, the term of this patent is extended or adjusted under 35 U.S.C. 154(b) by 132 days.

(21) Appl. No.: 09/801,964

(22) Filed: Mar. 8, 2001

(65) Prior Publication Data

US 2002/0002138 A1 Jan. 3, 2002

Related U.S. Application Data

(60) Provisional application No. 60/187,965, filed on Mar. 9, 2000.

(51) Int. Cl.[7] .................. A61K 38/05; A61K 38/14; C07K 5/06; C07K 9/00
(52) U.S. Cl. .............. 514/8; 514/19; 514/23; 514/303; 514/404; 536/17.4; 546/119; 546/120; 548/370.1
(58) Field of Search ................ 514/8, 19, 23, 514/303, 404; 536/17.4; 546/119, 120; 548/370.1

(56) References Cited

FOREIGN PATENT DOCUMENTS

WO    WO 9724369    7/1997    ............ C07K/5/06

*Primary Examiner*—Jeffrey E. Russel
(74) *Attorney, Agent, or Firm*—Peter C. Richardson; Gregg C. Benson; Carl J. Goddard

(57) ABSTRACT

The invention provides metabolites of the compound 2-amino-N-[2-(3a(R)-benzyl-2-methyl-3-oxo-2,3,3a,4,6,7-hexahydro-pyrazolo-[4,3-c]pyridin-5-yl)-1-(R)-benzyl-oxymethyl-2-oxo-ethyl]-isobutyramide, the racemic-diastereomeric mixtures and optical isomers thereof, the prodrugs thereof, and the pharmaceutically acceptable salts of the metabolites, racemic-diastereomeric mixtures, optical isomers, and prodrugs; to pharmaceutical compositions thereof; and to methods of using the metabolites and the compositions in the treatment of diseases associated with reduced levels of growth hormone.

The invention further provides a kit comprising a metabolite of the compound 2-amino-N-[2-(3a(R)-benzyl-2-methyl-3-oxo-2,3,3a,4,6,7-hexahydro-pyrazolo-[4,3-c]pyridin-5-yl)-1-(R)-benzyl-oxymethyl-2-oxo-ethyl]-isobutyramide a racemic-diastereomeric mixture or optical isomer thereof, a prodrug thereof, or a pharmaceutically acceptable salt of the metabolite, racemic-diastereomeric mixture, optical isomers, or prodrug, and a pharmaceutically acceptable carrier, vehicle or diluent in a first unit dosage form; estrogen, progesterone, Premarin®, or a bisphosphonate compound, preferably alendronate, and a pharmaceutically acceptable carrier, vehicle or diluent in a second unit dosage form; and a container.

34 Claims, No Drawings

HEXAHYDROPYRAZOLO[4,3,-C]PYRIDINE METABOLITES

CROSS REFERENCE TO RELATED APPLICATION

This application claims the benefit of U.S. Provisional Application No. 60/187,965 filed Mar. 9, 2000.

BACKGROUND OF THE INVENTION

The invention relates to metabolites of the compound 2-amino-N-[2-(3a(R)-benzyl-2-methyl-3-oxo-2,3,3a,4,6,7-hexahydro-pyrazolo-[4,3-c]pyridin-5-yl)-1-(R)-benzyl-oxymethyl-2-oxo-ethyl]-isobutyramide, pharmaceutical compositions thereof, and to methods of using the metabolites and the pharmaceutical compositions in the treatment of diseases associated with reduced levels of growth hormone.

Growth hormone (GH), which is secreted from the pituitary gland, stimulates the growth of all tissues in the body that are capable of growing. Additionally, GH is known to mediate the following basic effects on the metabolic processes of the body:

(1) increased rate of protein synthesis in substantially all cells of the body;
(2) decreased rate of carbohydrate utilization in cells of the body; and
(3) increased mobilization of free fatty acids and use thereof for energy.

Deficiency in growth hormone production results in a variety of medical disorders. In children, it causes dwarfism. In adults, the consequences of acquired GH deficiency include profound reduction in lean body mass and concomitant increase in total body fat, particularly in the truncal region. Decreased skeletal and cardiac muscle mass and muscle strength lead to a significant reduction in exercise capacity. Bone density is also reduced. Administration of exogenous GH has been shown to reverse many of these metabolic changes. Additional benefits of therapy have included reduction in LDL cholesterol and improved psychological well-being.

In cases where increased levels of GH were desired, the problem was generally solved by providing exogenous GH or by administering an agent which stimulated GH production or release. In either instance, the peptidyl nature of the compound necessitated that it be administered by injection. Initially, GH was obtained from extractions of the pituitary glands of cadavers. This resulted in an expensive product, and carried with it the risk that a disease associated with the source of the pituitary gland could be transmitted to the recipient of the GH (e.g. Jacob-Creutzfeld Disease). Recently, recombinant GH has become available which, while no longer carrying any risk of disease transmission, is still a very expensive product which must be administered by injection or by nasal spray.

Most GH deficiencies are caused by defects in GH release, not primary defects in the pituitary synthesis of GH. Therefore, an alternative strategy for normalizing serum GH levels is by stimulating its release from somatotrophs. Increasing GH secretion can also be achieved by stimulating or inhibiting various neurotransmitter systems in the brain and hypothalamus. As a result, the development of synthetic GH-releasing agents to stimulate pituitary GH secretion are being pursued, and may have several advantages over expensive and inconvenient GH replacement therapy. By acting along physiologic regulatory pathways, the most desirable agents would stimulate pulsatile GH secretion, and excessive levels of GH that have been associated with undesirable side effects of exogenous GH administration would be avoided by virtue of intact negative feedback loops.

Physiologic and pharmacologic stimulators of GH secretion include argine, L-3,4-dihydroxyphenylalanine (L-DOPA), glucagon, vasopressin, and insulin induced hypoglycemia, as well as activities such as sleep and exercise, indirectly cause GH to be released from the pituitary gland by acting in some fashion on the hypothalamus, perhaps either to decrease somatostatin secretion or to increase the secretion of the known secretagogue growth hormone releasing factor (GHRF), or an unknown endogenous GH-releasing hormone, or all three of these.

Other compounds have been developed which stimulate the release of exogenous GH such as analogous peptidyl compounds related to GHF or the peptides of U.S. Pat. No. 4,411,890. These peptides, while considerably smaller than growth hormones, are still susceptible to various proteases. As with most peptides, their potential for oral bioavailability is low. Additional GH secretagogues are disclosed in, inter alia, commonly assigned PCT International Application Publication No. WO97/24369, the disclosure of which is incorporated herein by reference, which refers to certain GH secretagogues of Formula A:

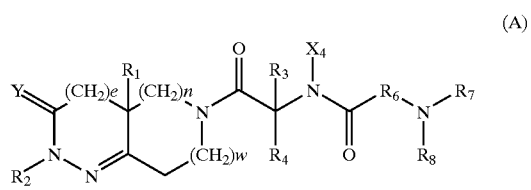

(A)

SUMMARY OF THE INVENTION

The instant invention provides metabolites of the compound of formula (I)

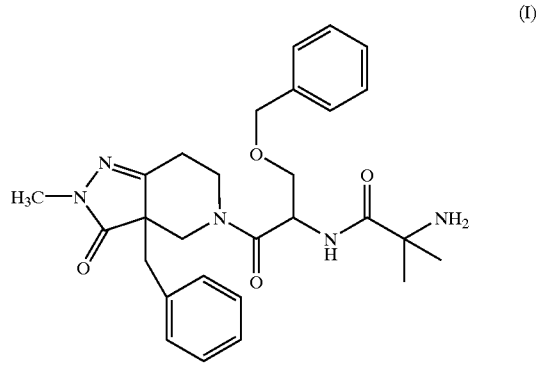

(I)

the racemic-diastereomeric mixtures and optical isomers thereof, prodrugs thereof, and the pharmaceutically acceptable salts of the metabolites, racemic-diastereomeric mixtures, optical isomers, and prodrugs; pharmaceutical compositions thereof; and to methods of treating disease states associated with reduced levels of growth hormone using the metabolites and pharmaceutical compositions.

DETAILED DESCRIPTION OF THE INVENTION

The instant invention provides metabolites of the compound of formula (I)

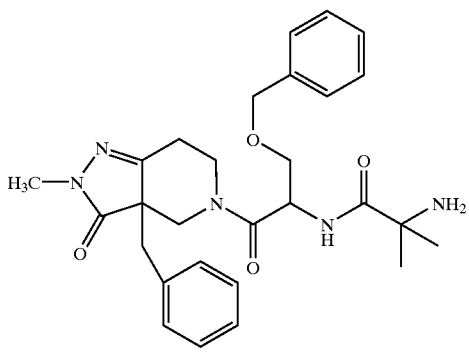

(I)

the racemic-diastereomeric mixtures and optical isomers thereof, prodrugs thereof, and the pharmaceutically acceptable salts of the metabolites, racemic-diastereomeric mixtures, optical isomers, and prodrugs, pharmaceutical compositions thereof; and to methods of treating diseases associated with reduced levels of growth hormone using the metabolites and pharmaceutical compositions.

The invention provides metabolites of the compound of structural formula (I) wherein the metabolites preferably comprise the acetylated, carboxylated, glucuronidated, and hydroxylated derivatives thereof.

A preferred acetylated metabolite derivative is the compound:

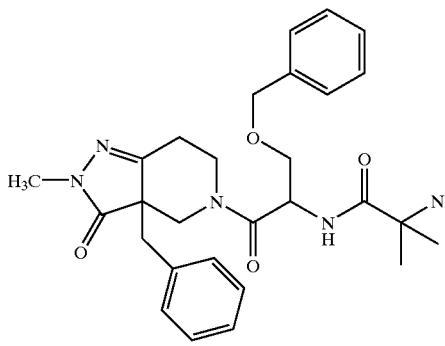

(Ia)

the racemic-diastereomeric mixtures and optical isomers thereof, prodrugs thereof, and the pharmaceutically acceptable salts of the metabolites, racemic-diastereomeric mixtures, optical isomers, and prodrugs, wherein the compound has an [MH]$^+$=m/z 549.

Preferred carboxylated metabolite derivatives are those compounds selected from the group consisting of:

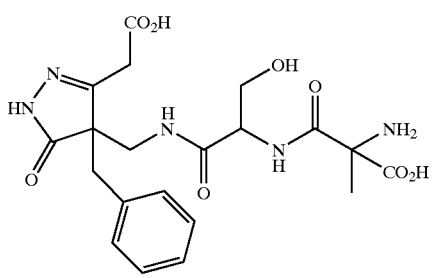

(Ib)

and

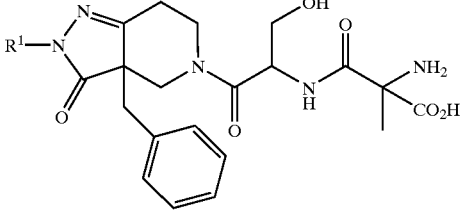

(Ic)

wherein R$^1$ is hydrogen or methyl; the racemic-diastereomeric mixtures and optical isomers thereof, prodrugs thereof, and the pharmaceutically acceptable salts of the metabolites, racemic-diastereomeric mixtures, optical isomers, and prodrugs, wherein:

(i) compound (Ib) has an [M+H]$^+$=m/z 464;
(ii) when R$^1$ is hydrogen in compound (Ic), the compound has an [M+H]$^+$=m/z 432; and
(iii) when R$^1$ is methyl in compound (Ic), the compound has an [M+H]$^+$=m/z 446.

Preferred glucuronidated metabolite derivatives are those compounds selected from the group consisting of:

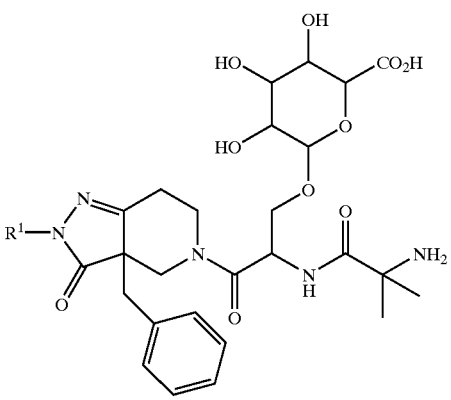

(Id)

wherein R$^1$ is hydrogen or methyl; the racemic-diastereomeric mixtures and optical isomers thereof, prodrugs thereof, and the pharmaceutically acceptable salts of the metabolites, racemic-diastereomeric mixtures, optical isomers, and prodrugs, wherein:

(i) when R$^1$ is hydrogen in compound (Id), the compound has an [M+H]$^+$=m/z 578; and
(ii) when R$^1$ is methyl in compound (Id), the compound has an [M+H]$^+$=m/z 592.

Preferred hydroxylated metabolite derivatives are those compounds selected from the group consisting of:

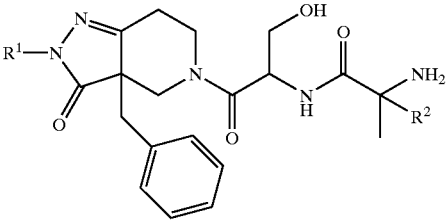

(Ie)

-continued

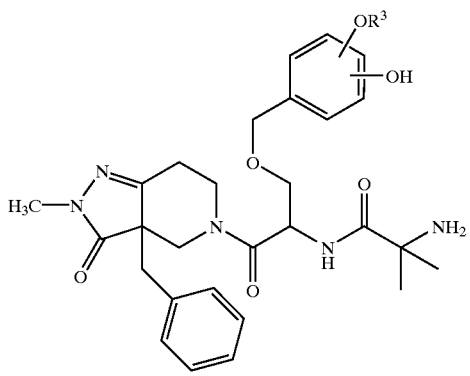

(If)

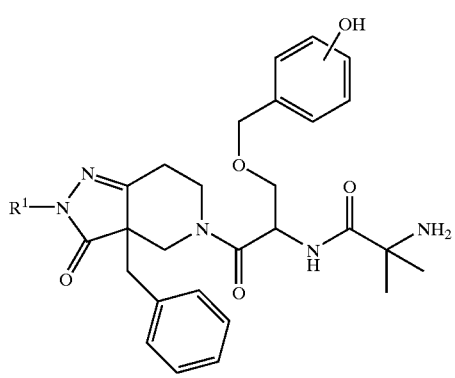

(Ig)

and

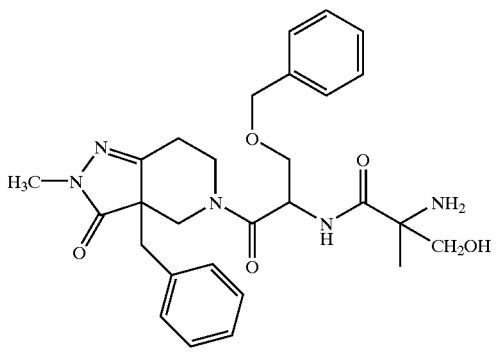

wherein R¹ is hydrogen or methyl, R² is methyl or $CH_2OH$, and R³ is hydrogen or methyl; the racemic-diastereomeric mixtures and optical isomers thereof, prodrugs thereof, and the pharmaceutically acceptable salts of the metabolites, racemic-diastereomeric mixtures, optical isomers, and prodrugs, wherein:

(i) when R¹ is hydrogen and R² is methyl in compound (Ie) the compound has an $[M+H]^+=m/z$ 402;

(ii) when R¹ and R² are both methyl in compound (Ie) the compound has an $[M+H]^+=m/z$ 416;

(iii) when R¹ is methyl and R² is $CH_2OH$ in compound (Ie), the compound has an $[M+H]^+=m/z$ 432;

(iv) when R¹ is hydrogen and R² is $CH_2OH$ in compound (Ie), the compound has an $[M+H]^+=m/z$ 418;

(v) when R³ is hydrogen in compound (If), the compound has an $[MH]^+=m/z$ 538;

(vi) when R³ is methyl in compound (If), the compound has an $[MH]^+=m/z$ 552;

(vii) when R¹ is hydrogen in compound (Ig), the compound has an $[MH]^+=m/z$ 508;

(viii) when R¹ is methyl in compound (Ig), the compound has an $[MH]^+=m/z$ 522; and (ix) compound (Ih) has an $[M+H]^+=m/z$ 522.

In a further embodiment of the instant invention, the metabolites of the compound of formula (I) are present in a substantially pure state or form.

The invention further provides:

(i) methods of increasing levels of endogenous growth hormone in a human or other animal which comprise administering to such human or animal an effective amount of a metabolite of the compound of formula (I), a racemic-diastereomeric mixture or optical isomer thereof, a prodrug thereof, or a pharmaceutically acceptable salt of said metabolite, racemic-diastereomeric mixture, optical isomer, or prodrug;

(ii) methods of treating or preventing osteoporosis in an animal which comprise administering to an animal an effective amount of a metabolite of the compound of formula (I), a racemic-diastereomeric mixture or optical isomer thereof, a prodrug thereof, or a pharmaceutically acceptable salt of said metabolite, racemic-diastereomeric mixture, optical isomer, or prodrug;

(iii) methods of treating or preventing diseases or conditions in an animal which may be treated or prevented by growth hormone, preferably congestive heart failure, frailty associated with aging, age-related decline in physical performance, or obesity, which comprise administering to an animal an amount of a metabolite of the compound of formula (I), a racemic-diastereomeric mixture or optical isomer thereof, a prodrug thereof, or a pharmaceutically acceptable salt of said metabolite, racemic-diastereomeric mixture, optical isomer, or prodrug, effective in promoting release of endogenous growth hormone;

(iv) methods of accelerating bone fracture repair, attenuating post-surgical protein catabolic response, reducing cachexia and protein loss due to chronic illness, accelerating wound healing, or accelerating the recovery of burn patients or patients having undergone major surgery, which comprise administering to an animal in need of such treatment an amount of a metabolite of the compound of formula (I), a racemic-diastereomeric mixture or optical isomer thereof, a prodrug thereof, or a pharmaceutically acceptable salt of said metabolite, racemic-diastereomeric mixture, optical isomer, or prodrug, which is effective in promoting release of endogenous growth hormone;

(v) methods of improving muscle strength, mobility, maintenance of skin thickness, metabolic homeostasis in an animal which comprise administering to an animal an amount of a metabolite of the compound of formula (I), a racemic-diastereomeric mixture or optical isomer thereof, a prodrug thereof, or a pharmaceutically acceptable salt of said metabolite, racemic-diastereomeric mixture, optical isomer, or prodrug, which is effective in promoting release of endogenous growth hormone;

(vi) methods of treating or preventing osteoporosis in an animal which comprise administering to said animal a bisphosphonate compound, preferably alendronate, and a metabolite of the compound of formula (I), a racemic-diastereomeric mixture or optical isomer thereof, a prodrug thereof, or a pharmaceutically acceptable salt of said metabolite, racemic-diastereomeric mixture, optical isomer, or prodrug;

(vii) methods of treating or preventing osteoporosis in an animal which comprise administering to said animal a combination of estrogen or Premarin®, a metabolite of the compound of formula (I), a racemic-diastereomeric mixture or optical isomer thereof, a prodrug thereof, or a pharmaceutically acceptable salt of said metabolite, racemic-diastereomeric mixture, optical isomer, or prodrug, and, optionally, progesterone;

(viii) pharmaceutical compositions useful for increasing the endogenous production or release of growth hormone in a human or other animal which comprise a metabolite of the compound of formula (I), a racemic-diastereomeric mixture or optical isomer thereof, a prodrug thereof, or a pharmaceutically acceptable salt of said metabolite, racemic-diastereomeric mixture, optical isomer, or prodrug, and a pharmaceutically acceptable carrier, vehicle, or diluent;

(ix) methods of increasing levels of endogenous growth hormone in an animal which comprise administering to the animal an effective amount of the composition comprising a metabolite of the compound of formula (I), a racemic-diastereomeric mixture or optical isomer thereof, a prodrug thereof, or a pharmaceutically acceptable salt of said metabolite, racemic-diastereomeric mixture, optical isomer, or prodrug;

(x) methods of treating or preventing diseases or conditions in an animal which may be treated or prevented by growth hormone, preferably congestive heart failure, frailty associated with aging, age-related decline in physical performance, or obesity, which comprise administering to the animal in need of such treatment an amount of the composition comprising a metabolite of the compound of formula (I), a racemic-diastereomeric mixture or optical isomer thereof, a prodrug thereof, or a pharmaceutically acceptable salt of said metabolite, racemic-diastereomeric mixture, optical isomer, or prodrug effective in promoting the release of growth hormone;

(xi) methods of accelerating bone fracture repair, attenuating post-surgical protein catabolic response, reducing cachexia and protein loss due to chronic illness, accelerating wound healing, or accelerating the recovery of burn patients or patients having undergone major surgery, which comprise administering to an animal in need of such treatment an amount of the composition comprising a metabolite of the compound of formula (I), a racemic-diastereomeric mixture or optical isomer thereof, a prodrug thereof, or a pharmaceutically acceptable salt of said metabolite, racemic-diastereomeric mixture, optical isomer, or prodrug effective in promoting the release of growth hormone;

(xii) methods of improving muscle strength, mobility, maintenance of skin thickness, metabolic homeostasis in an animal in need thereof, which comprise administering to an animal an amount of the composition comprising a metabolite of the compound of formula (I), a racemic-diastereomeric mixture or optical isomer thereof, a prodrug thereof, or a pharmaceutically acceptable salt of said metabolite, racemic-diastereomeric mixture, optical isomer, or prodrug effective in promoting the release of growth hormone; and (xiii) methods of treating or preventing osteoporosis in an animal which comprise administering to an animal in need of such treatment an amount of the composition comprising a metabolite of the compound of formula (I), a racemic-diastereomeric mixture or optical isomer thereof, a prodrug thereof, or a pharmaceutically acceptable salt of said metabolite, racemic-diastereomeric mixture, optical isomer, or prodrug effective in promoting the release of growth hormone, and, optionally, progesterone.

Additionally, the metabolites of the instant invention are useful as markers or standards for assessing the metabolic fate of the compound of formula (I) in an animal species, including humans.

While not specifically denoted in the generic formula (I), the metabolites of the invention will all have at least one asymmetric center. Additional asymmetric centers may be present in the molecule depending upon the nature of the various substituents present in the molecule. Each such asymmetric center will produce two optical isomers and it is to be understood that all such optical isomers, as separated, pure or partially purified optical isomers, racemic mixtures or diastereomeric mixtures thereof, be included within the scope of the instant invention.

The expression "prodrug", as employed throughout the description and appendant claims, refers to compounds that are drug precursors which, following administration, release the drug in vivo via a chemical or physiological process (e.g. a prodrug on being brought to physiological pH is converted to the desired drug form). Exemplary prodrugs, for example, release the corresponding free carboxylic acid, and such hydrolyzable ester-forming residues of the metabolites of the invention include, but are not limited to, carboxylic acid metabolites wherein the free hydrogen atom is replaced by $(C_1-C_6)$alkyl, $(C_2-C_{12})$alkanoylmethyl, $(C_4-C_9)$-1-(alkanoyloxy)ethyl, 1-methyl-1-(alkanoyloxy)-ethyl having from 5 to 10 carbon atoms, alkoxycarbonyloxymethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, γ-butyrolacton-4-yl, di-N,N-$(C_1-C_2)$alkylamino$(C_2-C_3)$ alkyl (such as β-dimethylaminoethyl), carbamoyl-$(C_1-C_2)$ alkyl, N,N-di$(C_1-C_2)$alkylcarbamoyl-$(C_1-C_2)$alkyl and piperidino-, pyrrolidino-, or morpholino$(C_1-C_2)$alkyl.

Prodrugs of the invention where the carboxyl group in a carboxylic acid functionality has been derivatized as an ester may be prepared by combining the carboxylic acid with an appropriate alkyl halide in the presence of a base such as potassium carbonate in a reaction-inert solvent such as DMF at a temperature of about 0° C. to about 100° C. for about 1 to about 24 hours. Alternatively, the acid may be combined with an appropriate alcohol as the solvent in the presence of a catalytic amount of an acid such as concentrated sulfuric acid at a temperature of about 20° C. to about 120° C., preferably at reflux, for about 1 hour to about 24 hours. Another method is to react the acid in an inert solvent such as THF, with concomitant removal of the water being produced by physical (e.g. a Dean-Stark trap), or chemical (e.g. molecular sieves) means.

Other exemplary prodrugs release an alcohol wherein the free hydrogen atom of the hydroxyl substituent of the metabolite is replaced by $(C_1-C_6)$alkanoyloxymethyl, 1-($(C_1-C_6)$alkanoyloxy)ethyl, 1-methyl-1-($(C_1-C_6)$ alkanoyloxy)ethyl, $(C_1-C_6)$alkoxycarbonyloxymethyl, N-$(C_1-C_6)$alkoxycarbonylaminomethyl, succinoyl, $(C_1-C_6)$ alkanoyl, α-amino$(C_1-C_4)$alkanoyl, arylacetyl, and α-aminoacyl, or α-aminoacyl-α-aminoacyl wherein the α-aminoacyl moieties are independently any of the naturally occurring L-amino acids found in proteins, —P(O)(OH)$_2$, —P(O)(O$(C_1-C_6)$alkyl)$_2$, or glycosyl (e.g. the radical resulting from detatchment of the hydroxyl of the hemiacetal of a carbohydrate).

Prodrugs of the invention where an alcohol functionality has been derivatized as an ether may be prepared by combining the alcohol with an appropriate alkyl bromide or iodide in the presence of a base such as potassium carbonate in a reaction-inert solvent such as DMF at a temperature of about 0° C. to about 100° C. for about 1 to about 24 hours. Alkanoylaminomethyl ethers may be obtained by reaction of the alcohol with a bis-(alkanoylamino)methane in the presence of a catalytic amount of acid in a reaction-inert solvent such as THF, according to the method described in U.S. Pat. No. 4,997,984. Alternatively, these compounds may be prepared according to the methods described by Hoffman et al., in J. Organic Chem., 59, 3530 (1994).

The pharmaceutically acceptable acid addition salts of the metabolites of the invention generally comprise, for example, those salts derived from using both organic and inorganic acids. Examples of such acids include hydrochloric, nitric, sulfuric, phosphoric, formic, acetic, trifluoroacetic, propionic, maleic, succinic, D-tartaric, L-tartaric, malonic, methanesulfonic, and the like. In addition, the metabolites containing a carboxylic acid functionality may form basic addition salts with certain inorganic counter-ions, for example, sodium, potassium, lithium, calcium, magnesium, and the like as well as those formed from organic bases.

The pharmaceutically acceptable salts may be formed by taking about 1 equivalent of the metabolite and contacting it with about 1 equivalent of the appropriate corresponding desired acid or base. Workup and isolation of the resulting salt may be effected by means that will be well-known to one of ordinary skill in the art in light of the instant disclosure.

The metabolites of the compound of formula (I), the racemic-diastereomeric mixtures and optical isomers thereof, prodrugs thereof, and the pharmaceutically acceptable salts of the metabolites, racemic-diastereomeric mixtures, optical isomers, and prodrugs are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the metabolites of the invention can be used in the evaluation of how other hormones modify growth hormone releasing activity. For example, it has already been established that somatostatin inhibits growth hormone release.

The metabolites of the compound of formula (I), the racemic-diastereomeric mixtures and optical isomers thereof, prodrugs thereof, and the pharmaceutically acceptable salts of the metabolites, racemic-diastereomeric mixtures, optical isomers, and prodrugs can be administered to animals, including humans, to release growth hormone in vivo. The metabolites may be used to treat symptoms related to growth hormone deficiency, stimulate growth or enhance feed efficiency of animals raised for meat production to improve carcass quality, to increase milk production in dairy cattle, to improve bone or wound healing and improvement in vital organ function. The metabolites of the invention, by inducing endogenous growth hormone secretion, will alter body composition and modify other growth hormone-dependent metabolic, immunologic, or developmental processes. For example, the metabolites of the invention can be given to chickens, turkeys, livestock animals (such as sheep, pigs, horses, cattle, etc.), companion animals (such as dogs, cats, etc.), or may have utility in aquaculture to accelerate growth and improve protein/fat ratio. In addition, the metabolites can be administered to humans in vivo as a diagnostic tool to directly determine whether the pituitary is capable of releasing growth hormone. For example, the metabolites can be administered in vivo to children. Serum samples taken before and following such administration can be assayed for growth hormone. Comparison of the amounts of growth hormone in each of these samples would comprise a means for directly determining the ability of the patient's pituitary to release growth hormone.

The metabolites of the invention, the racemic-diastereomeric mixtures and optical isomers thereof, prodrugs thereof, and the pharmaceutically acceptable salts of the metabolites, racemic-diastereomeric mixtures, optical isomers, and prodrugs may be administered by oral, parenteral (e.g. intramuscular, intraperitoneal, intravenous or subcutaneous injection, or implant), nasal, vaginal, rectal, sublingual, or topical routes of administration and can be formulated with pharmaceutically acceptable carriers, vehicles, or diluents to provide dosage forms appropriate for each intended route of administration.

Solid dosage forms for oral administration may include, for example, capsules, tablets, pills, powders, and granules. In such solid dosage forms, the active compound is admixed with at least one inert pharmaceutically acceptable carrier or diluent such as sucrose, lactose, or starch. Such dosage forms may also comprise, as is normal practice, additional substances other than such inert carriers or diluents, e.g. lubricating agents such as magnesium stearate. In the case of capsules, tablets and pills, the dosage forms may also comprise buffering agents. Tablets and pills may additionally be prepared with enteric coatings.

Liquid dosage forms for oral administration include pharmaceutically acceptable emulsions, solutions, suspensions, and syrups, the elixirs formed thereby containing inert diluents commonly utilized in the art, such as water. In addition to such inert diluents, compositions may also comprise adjuvants, such as wetting agents, emulsifying and suspending agents, and sweetening, flavoring, and perfuming agents.

Preparations for parenteral administration may include sterile aqueous or non-aqueous solutions, suspensions, or emulsions. Examples of non-aqueous solvents or vehicles comprise propylene glycol, polyethylene glycol, vegetable oils, such as olive oil and corn oil, gelatin, and injectable organic esters, such as ethyl oleate. Such dosage forms may also comprise adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions that can be dissolved in sterile water, or some other sterile injectable medium immediately before use.

The metabolites of the invention, the racemic-diastereomeric mixtures and optical isomers thereof, prodrugs thereof, and the pharmaceutically acceptable salts of the metabolites, racemic-diastereomeric mixtures, optical isomers, and prodrugs may also be encapsulated in liposomes to permit the intravenous administration thereof. The liposomes suitable for use in this intention may include lipid vesicles and comprise plurilamellar lipid vesicles, small sonicated multilamellar vesicles, reverse phase evaporation vesicles, large multilamellar vesicles, and the like, wherein the lipid vesicles are formed by one or more phospholipids such as phospotidylcholine, phosphatidylcholine, sphingomyelin, phospholactic acid, and the like. In addition, the vesicles may also comprise a sterol component such as cholesterol.

Compositions for rectal or vaginal administration are preferably suppositories which may contain, in addition to the active substance, excipients such as coca butter, or a suppository wax.

Compositions for nasal or sublingual administration may also be prepared with standard excipients that will be well-known to one of ordinary skill in the art.

Additional methods of preparing various pharmaceutical compositions with a desired amount of an active ingredient are known, or will be apparent in light of this disclosure, to one of ordinary skill in the art. See, for example, Remington's Pharmaceutical Sciences, Mack Publishing Company, Easton, Pa., 18th Edition (1990).

The dosage of the metabolites, the racemic-diastereomeric mixtures and optical isomers thereof, prodrugs thereof, and the pharmaceutically acceptable salts of the metabolites, racemic-diastereomeric mixtures, optical isomers, and prodrugs may be varied, however, it is necessary that the amount thereof be such that a suitable dosage is provided. The selected dosage depends on the desired therapeutic effect, on the route of administration, and on the duration of treatment. Generally, representative dosage levels of from about 0.0001 to about 100 mg/kg of body weight per day may be administered to humans and other animals, e.g. mammals, to obtain effective release of GH.

A preferred dosage range is from about 0.01 to about 5.0 mg/kg of body weight daily which can be administered as a single dose or divided into multiple doses. The ability to select an appropriate dosage level of a metabolite of the compound of formula (I) according to the methods of the invention is within the purview of one of ordinary skill in the art having benefit of the instant disclosure. Generally, treatment is initiated with smaller dosages that are less than the optimum dose of the compound. Thereafter, the dosage is increased incrementally until the optimum effect under the individual circumstances is achieved.

Since the instant invention relates to the treatment of disease states associated with reduced levels of growth hormone with a combination of active ingredients that may be administered separately, the invention also relates to combining separate pharmaceutical compositions in kit form. A kit, according to the invention, comprises two separate pharmaceutical compositions: a first unit dosage form comprising a metabolite of the compound of formula (I), a racemic-diastereomeric mixture or optical isomer thereof, a prodrug thereof, or a pharmaceutically acceptable salt of the metabolite, racemic-diastereomeric mixture, optical isomers, or prodrug, and a pharmaceutically acceptable carrier, vehicle or diluent; a second unit dosage form comprising estrogen, progesterone, Premarin®, or a bisphosphonate compound, preferably alendronate, and a pharmaceutically acceptable carrier, vehicle or diluent; and a container. The container is used to contain the separate pharmaceutical compositions and may comprise, for example, a divided bottle or a divided foil packet, however, the separate pharmaceutical compositions may also be contained within a single, undivided container. Normally, the kit will also include directions for the administration of the separate components. The kit form is particularly advantageous when the separate components are preferably administered in different dosage forms (e.g., oral and parenteral), are administered at different dosage levels, or when titration of the individual components of the combination is desired by the prescribing physician.

One example of such a kit comprises a so-called blister pack. Blister packs are well known in the packaging industry and are being widely used for the packaging of pharmaceutical unit dosage forms (tablets, capsules, and the like). Blister packs generally comprise a sheet of relatively rigid material covered with a foil of a preferably transparent plastic material. During the packaging process, recesses are formed in the plastic foil. The recesses generally conform to the size and shape of the tablets or capsules to be contained therein. Next, the tablets or capsules are placed in the recesses and the sheet of relatively rigid material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules may be removed from the blister pack by the application of manual pressure on the recesses, preferably by the fingers of the user thereof, whereby an opening is formed in the sheet at the place of the recess. The tablet or capsule can then be removed through the formed opening.

It is further desirable to provide a memory aid on the pack, e.g., in the form of numbers or similar indicia next to the tablets or capsules whereby the indicia correspond with the days of the regimen which the dosage form so specified is to be ingested. An additional example of such a memory aid is a calendar printed on the pack, e.g., as follows "First Week, Monday, Tuesday, . . . etc. . . . Second Week, Monday, Tuesday, . . . " etc. Other variations will be readily apparent. A "daily dose" can be a single tablet or capsule, or multiple tablets or capsules to be ingested on a given day. Also, a daily dose comprising a metabolite of the compound of formula (I), a racemic-diastereomeric mixture or optical isomer thereof, a prodrug thereof, or a pharmaceutically acceptable salt of the metabolite, racemic-diastereomeric mixture, optical isomers, or prodrug can consist of one tablet or capsule, while a daily dose comprising estrogen, progesterone, Premarin®, or a bisphosphonate compound, preferably alendronate, can consist of multiple tablets or capsule, or vice versa. The memory aid should reflect this.

In another specific embodiment of the invention, a pack designed to dispense the daily doses one at a time in the order of their intended use is provided. Preferably, the pack is equipped with a memory aid, so as to further facilitate compliance with the dosage regimen. An example of such a memory aid is a mechanical counter which indicates the number of daily doses to be dispensed. Another example of such a memory aid is a battery-powered micro-chip memory coupled with a liquid crystal readout, or audible reminder signal which, for example, reads out the date that the last daily dose has been taken and/or reminds the patient when the next dose is to be taken.

The compound of formula (I), also known as 2-amino-N-[2-(3a(R)-benzyl-2-methyl-3-oxo-2,3,3a,4,6,7-hexahydro-pyrazolo-[4,3-c]pyridin-5-yl)-1-(R)-benzyl-oxymethyl-2-oxo-ethyl]-isobutyramide, may be prepared according to the synthetic methodologies disclosed in the aforementioned commonly assigned International Patent Application Publication No. WO 97/24369.

Preparation of $^{14}$C-Radiolabelled (I)

The $^{14}$C-radiolabelled compound 2-amino-N-[2-(3a(R)-benzyl-2-methyl-3-oxo-2,3,3a,4,6,7-hexahydro-pyrazolo-[4,3-c]pyridin-5-yl)-1-(R)-benzyl-oxymethyl-2-oxo-ethyl]-isobutyramide, was prepared according to the following synthetic schemes.

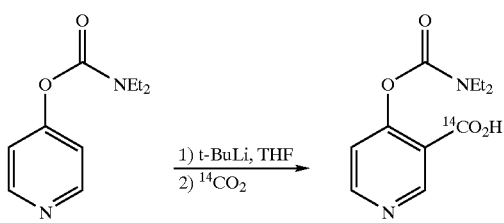

Compound (ii)

A solution of (i) (0.66 g, 3.4 mmol, 2 eq) in tetrahydrofuran (15 mL, distilled from lithium aluminum hydride) was cooled to −78° C. tert-Butyllithium (1.7 mL, 2.66 mmol, 1.5 eq, 1.5 M in pentane) was added dropwise. The cloudy, brownish-orange colored reaction mixture was stirred at −78° C. for 15 minutes, then frozen solid in a liquid nitrogen bath. [$^{14}$C]$CO_2$ (98.3 mCi, 57 mCi/mmol) was then vacuum transferred into the frozen reaction flask. The reaction was warmed to −78° C., stirred for 15 minutes, quenched with ethanol (5 mL), and allowed warm to room temperature. The reaction mixture was concentrated in vacuo and dissolved in ethanol (20 mL) to give 91.2 mCi (93% recovery of radioactivity) of (ii). Thin-layer chromatographic analysis (silica gel, 10% MeOH/CHCl$_3$) showed baseline material.

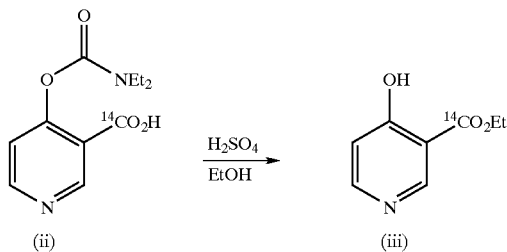

Compound (iii)

Crude (ii) (91.2 mCi) as a solution in ethanol (20 mL) was treated with concentrated sulfuric acid (0.5 mL). This clear, slightly yellow colored solution was heated to reflux and monitored by thin-layer chromatography (silica gel, 10% MeOH/CHCl$_3$). The reaction mixture was allowed to cool to room temperature and concentrated in vacuo. The residue was dissolved in water (25 mL) and then brought to pH 7.0 with 1N NaOH. The aqueous layer was then continually extracted with chloroform or chloroform/isopropanol (9/1). The combined organic layers were concentrated, and the residue was purified by silica gel chromatography (gradient, 10/0-9/1 chloroform/methanol) to give 71 mCi of (iii).

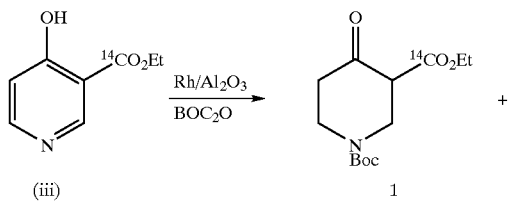

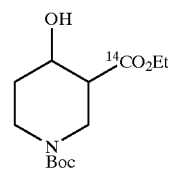

Compound 1

To a solution of (iii) (15.6 mCi, 0.27 mmol, 1 eq) in ethanol (8 mL) was added BOC$_2$O (0.12 g, 0.55 mol, 2 eq) and rhodium on alumina. The reaction was evacuated and back-flushed with hydrogen, fitted with a hydrogen balloon, and allowed to stir at room temperature while monitoring by thin-layer chromatography (3% MeOH/CHCl$_3$). Upon reaction completion, the reaction mixture was concentrated in vacuo, the residue filtered through a plug of silica gel (3% MeOH/CHCl$_3$), and purified by silica gel chromatography (20% EtOAc/hexanes) to give 6.71 mCi of 1.

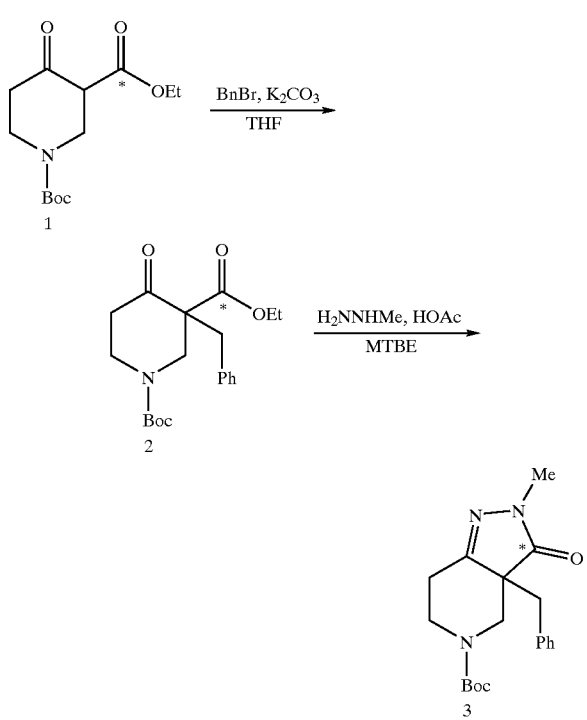

Compound 2

To a solution of 1 (94.7 mCi, 1.67 mmol) in tetrahydrofuran (5 mL) was added potassium carbonate (580 mg, 4.19 mmol, 2.5 eq) and benzyl bromide (0.30 mL, 2.52 mmol, 1.5 eq). The solution was heated to 60° C. under a N$_2$ atmosphere for 24 hours, after which time the solution was filtered and concentrated in vacuo. The residue was purified by silica gel chromatography (10% ethyl acetate/hexanes) to yield 85.8 mCi of 2.

Compound 3

To a solution of 2 (115.8 mCi, 2.05 mmol) in methyl tert-butyl ether (5 mL) was added methylhydrazine (0.13 mL, 2.45 mmol, 1.2 eq) and glacial acetic acid (0.18 mL, 3.07 mmol, 1.5 eq). The solution was heated to 60° C. under a N$_2$ atmosphere for 27 hours, after which time an additional 0.13 mL methylhydrazine (2.45 mmol, 1.2 eq) and 0.10 mL glacial acetic acid (1.75 mmol, 0.85 eq) were added. The solution was stirred at 60° C. under a N$_2$ atmosphere for 19 hours, after which time the solution was cooled and ethyl acetate (20 mL) was added. The solution was washed with saturated sodium bicarbonate (2×5 mL), dried over sodium sulfate, filtered, and concentrated in vacuo. The residue was purified by silica gel chromatography (20% ethyl acetate/hexanes) to yield 22.4 mCi of 3.

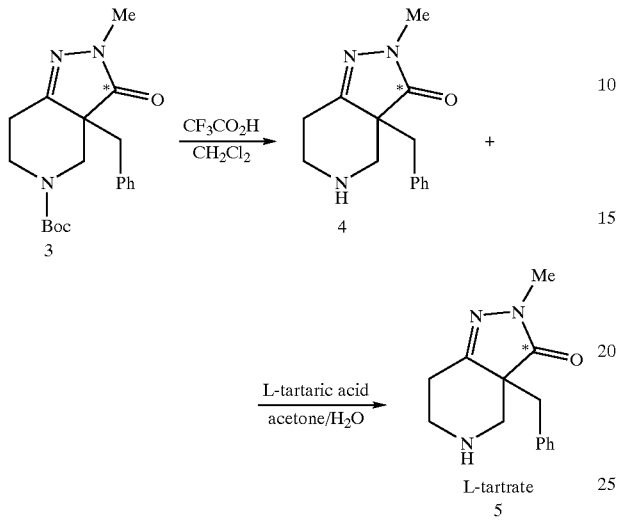

Compound 4

To a solution of 3 (32.0 mCi, 0.57 mmol) in dichloromethane (2 mL) cooled to 0° C. under a $N_2$ atmosphere was added trifluoroacetic acid (0.45 mL, 5.84 mmol, 10.2 eq). The solution was stirred at 0° C. under a $N_2$ atmosphere for 2 hours, after which time another 0.45 mL trifluoroacetic acid (5.84 mmol, 10.2 eq) was added. The solution was stirred for an additional 4 hours at 0° C. under a $N_2$ atmosphere, and then allowed to warm to room temperature. The solution was diluted with dichloromethane (15 mL), washed with saturated sodium bicarbonate (2×8 mL), dried over sodium sulfate, filtered, and concentrated in vacuo to yield 24.9 mCi of crude 4. The crude product was used directly in the next reaction.

Compound 5

To a solution of 4 (24.9 mCi, 0.44 mmol) in 8:1 acetone/water (3 mL) was added L-tartaric acid (73 mg, 0.49 mmol, 1.1 eq). The solution was heated to 50° C. under a $N_2$ atmosphere for 17 hours, after which time the solution was cooled to 0° C. and stirred for an additional 2.5 hours. The solution was filtered and the solids were washed with cold 8:1 acetone/water (5×2 mL). The solids were dried in a vacuum dessicator at room temperature for 17 hours to yield 16.3 mCi of 5.

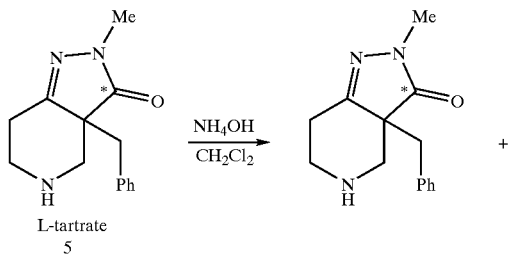

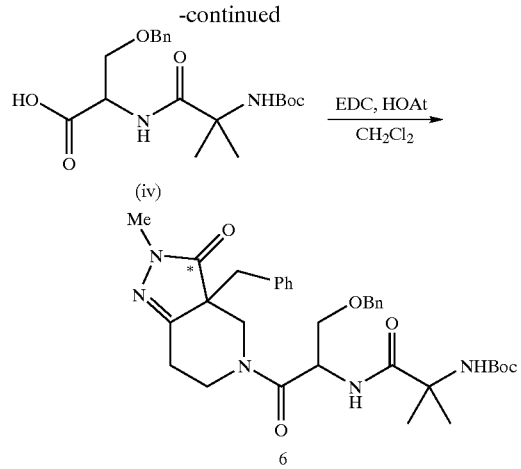

Compound 6

To a solution of 5 (1.8 mCi, 0.03 mmol) in dichloromethane (2 mL) at −40° C. under a $N_2$ atmosphere was added ammonium hydroxide (0.01 mL, 0.15 mmol). The solution was stirred 1 hour, after which time the solution was filtered through a sintered glass funnel into a second reaction vessel at −40° C. To this solution was added compound iv, prepared as described in the aforementioned International Patent Application Publication No. WO 97/24369, (36 mg, 0.09 mmol, 3.0 eq), 1-hydroxy-7-azabenzotriazole (13 mg, 0.09 mmol, 3.0 eq), and 1-(3-dimethylaminopropyl)-3-ethylcarbodiimide hydrochloride (18 mg, 0.09 mmol, 3.0 eq). The solution was warmed to 0° C. and stirred under a $N_2$ atmosphere for 3 hours. The solution was diluted with dichloromethane (10 mL), washed with water (2×6 mL), dried over sodium sulfate, and concentrated in vacuo to yield 1.8 mCi of crude 6.

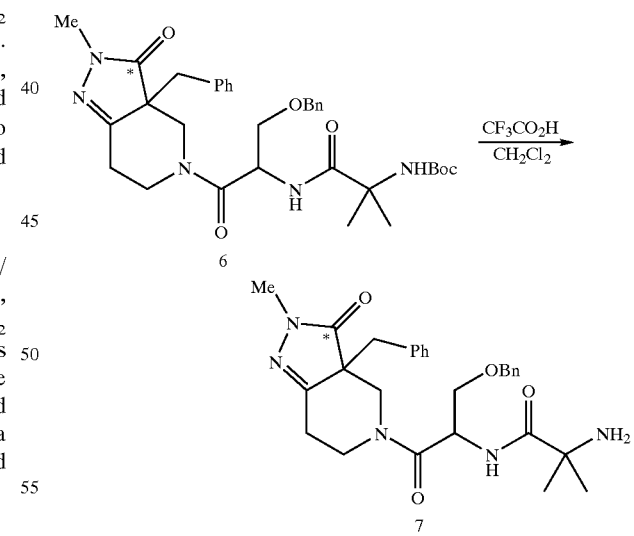

Compound 7

To a solution of 6 (11.34 mCi, 0.20 mmol) in dichloromethane at 0° C. under a $N_2$ atmosphere was added trifluoroacetic acid (0.50 mL, 6.5 mmol, 32 eq). The solution was stirred for 7 hours, after which point it was allowed to warm to room temperature. After stirring for an additional 1 hour, the solution was diluted with dichloromethane (20 mL), washed with saturated sodium bicarbonate (2×5 mL), brine (5 mL), dried over sodium sulfate, and concentrated in

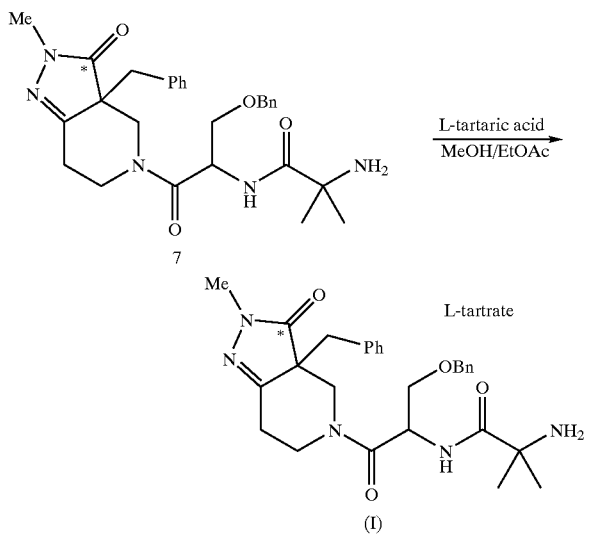

Compound (I)

To a solution of $^{14}$C-radiolabelled 7 (4.87 mCi, 0.09 mmol) and non-$^{14}$C-radiolabelled 7 (932.6 mg, 1.84 mmol) in ethyl acetate (26 mL) was added a solution of L-tartaric acid (290.3 mg, 1.93 mmol, 1.0 eq) in methanol (8 mL). The solvent was reduced in vacuo, 20 mL ethyl acetate was added, and the solution was refluxed at 85° C. for 4 hours. The solution was allowed to cool to room temperature over 1 hour, after which time the solution was filtered and the solids were washed with ethyl acetate (3×10 mL). The solids were dried in a vacuum dessicator at room temperature for 17 hours to yield 1.17 g of compound (I).

Metabolite Isolation

The metabolites of the compound of formula (I) were isolated from urine and fecal samples of humans, mice, or rats utilizing the following procedures.

Metabolite Isolation from Human Subjects (Method A)

The testing dose was prepared by dissolving a hand-milled, uniform powder of the $^{14}$C-radiolabelled compound (tartrate salt; specific activity=4.73 μCi/mg free base equivalent; radiochemical purity>99.5%; chemical purity>99.5%) in water. A single 20 mg dose of the $^{14}$C-radiolabelled compound having a specific activity of 5.0 μCi/mg was then administered orally to each subject.

Four healthy male human subjects between the ages of 18–45 years participated in the study. Subjects were confined under continuous medical observation for at least twelve hours prior to dosing. All subjects fasted for at least eight hours prior to morning dosing. Subjects were required to refrain from becoming supine during the first four hours after dosing in order to standardize experimental conditions, and were also required to fast during the first four hours following compound administration. The compound was administered as a single 20 mg (free base equivalent; 100 μCi/subject) oral dose.) Following dosing, urine samples were collected for eight days at 0–24, 24–48, 48–72, 72–96, 96–120, 120–144, 144–168, and 168–192 hours post-dose. The urine samples were thoroughly mixed and the total volume of urine voided during these intervals was recorded. Feces were collected as passed from the time of dosing until 192 hours post-dose.

Radioactivity in urine was measured by liquid scintillation counting. The total radioactivity in urine was quantified directly in triplicate aliquots of 0.2 ml for each sampling timepoint. Samples were combined with Ecolite scintillation cocktail (ICN; Costa Mesa, Calif.) (5 ml) and counted using a Wallac Liquid Scintillation Counter Model #1409 (Wallac; Turku, Finland).

Feces collected at each sampling time were placed directly into tared stomacher bags and hydrated with water before storage at −20° C. Homogenous fecal slurries were prepared using a stomacher. The total weight of the fecal slurries was recorded for each timepoint. Triplicate aliquots (50–100 mg) of each slurry were weighed into oxidizer sample cups and dried overnight before combustion. The samples were oxidized using a Packard Model 307 oxidizer (R. J. Harvey Instrument Corp.; Downer's Grove, Ill.). Liberated $^{14}CO_2$ was trapped, scintillation cocktail was added, and the samples were counted. All samples were counted on the Wallac counter using an internal quench curve and a 2 sigma value of 4 (95% confidence). Burning efficiencies were >95% throughout the sample oxidation process.

Pre-dose urine and fecal samples were counted to determine the background count rate for each matrix. The amount of radioactivity in each matrix was expressed as a percentage of the total amount of radioactivity administered to each subject. The lower limit of quantitation (LLOQ) was considered to be twice the background.

Urine samples containing the highest levels of radioactivity were pooled for each subject and concentrated by lyophilization. The residues were reconstituted in 200 μl of acetonitrile:10 mM ammonium formate containing 1% formic acid (10:90). Radioactivity recovery from lyophilization and reconstitution ranged from 89 to 105%.

Fecal homogenates containing the highest levels of excreted radioactivity were pooled relative to excreted volume/mass at each timepoint. Pooled fecal homogenates were extracted with two acetonitrile washings (3 ml/g), and concentrated overnight under a nitrogen stream. Concentrated fecal extracts were reconstituted in 100 μl of acetonitrile: 10 mM ammonium formate, 1% formic acid (10:90) prior to analysis. Recoveries of radioactivity from the pooled fecal samples following extraction ranged from 89 to 109%.

Radiolabelled material in urine and feces, was analyzed by reverse phase HPLC. The HPLC system consisted of a gradient pump and a β-radioactivity detector (β-RAM; INUS; Tampa, Fla.) equipped with a 500 μl flow cell. Chromatography was carried out on a Zorbax (Palo Alto, Calif.) Rx C-18 column (4.6 mm×150 mm; 5 μm) utilizing a binary gradient of a mobile phase consisting of a mixture of 10 mM ammonium formate, 1% formic acid (Solvent A) and acetonitrile (Solvent B). The flow rate was 1.0 ml/min and the separation was achieved at ambient temperature. The gradient for the separation of metabolites in all of the matrices was programmed as follows: Solvent A:Solvent B; 90:10 changed to 60:40 from 0 to 30 min. The column was allowed to equilibrate to 90:10 buffer:acetonitrile for 10 min before the next injection. For all matrices, the recovery off of the column was>95%.

Metabolite Isolation from Mice (Method B)

The testing dose was prepared by combining a uniform powder of 2-amino-N-[2-(3a(R)-benzyl-2-methyl-3-oxo-2,3,3a,4,6,7-hexahydro-pyrazolo-[4,3-c]pyridin-5-yl)-1-(R)-benzyl-oxymethyl-2-oxo-ethyl]-isobutyramide (tartrate salt; specific activity=4.97 μCi/mg free base equivalent; radiochemical purity >99.5%; chemical purity >99.5%), $^{14}$C- radiolabelled as described hereinabove, in a solution of 100% nanopure water. The $^{14}$C-radiolabelled material was cut with unlabeled material to achieve 200 mg/kg of the base equivalent (10–12 µCi/mouse).

For mass balance studies, 18 mice (~25–30 g) were dosed and housed in metabolism cages (3 animals/sex/cage) to facilitate separate urine and feces collection. The dosing solution was mixed well by hand, vortexed, and allowed to stir. All animals were dosed by oral gavage following an overnight fast, each receiving a 200 mg/kg (free base equivalent) oral dose of $^{14}$C-radiolabeled material (10–12 µCi/mouse). The test animals were permitted ad libitum access to food throughout acclimation and testing periods.

Following administration of the $^{14}$C-radiolabelled test compound, urine and feces were quantitatively collected into pre-weighed sample containers for mass balance and metabolite identification. Urine and feces were collected just prior to dosing and at 0–24, 24–48, 48–72, 72–96, 96–120, 120–144, and 144–168 hr intervals post-dose and stored at −20° C. until further processing and analysis. Cage rinses were collected after each time point and a final rinse with isopropanol/water (1:1). The samples were analyzed for radioactivity and metabolite identification.

The total radioactivity in urine and cage rinse was quantified directly in triplicate aliquots for each sampling point.

Feces collected at each sampling time were hydrated with water, homogenized to uniform slurry, and recorded for each time point. Triplicate aliquots (25–50 mg) of each slurry were weighed into oxidizer sample cups and dried overnight before combustion. The samples were oxidized using a Packard Model 307 oxidizer. Liberated $^{14}CO_2$ was trapped, scintillation cocktail was added, and the samples were counted by liquid scintillation counting. All samples were counted using an internal quench and a 2 sigma error of $\leq 2\%$ or for a maximum of ten minutes.

Pre-dose urine and fecal samples were counted to determine the background count rate for each matrix. The amount of radioactivity in each matrix was expressed as µg-eq/ml and was calculated by using the specific activity of the dose administered. The lower limit of quantitation (LLOQ) was considered to be twice the background rate.

Urine and fecal homogenate samples were pooled relative to excreted volume/mass at each time point so that essentially 100% of excreted radioactivity was accounted for. Pooled urine was analyzed directly following centrifugation at 3500 rpm for ten minutes to remove precipitated material. Pooled fecal homogenates were extracted with two acetonitrile washings (3 ml/g), and concentrated overnight under nitrogen stream.

Quantification of metabolites was performed by measuring the radioactivity in the individual peaks that were separated on HPLC using β-RAM. The HPLC system consisted of a gradient pump and a β-radioactivity detector equipped with a 500 µl flow cell. Chromatography was carried out on a Zorbax Rx C-18 column (4.6 mm×150 mm; 3 µm) utilizing a binary gradient of a mobile phase consisting of a mixture of 10 mM ammonium formate containing 1% formic acid (Solvent A) and acetonitrile (Solvent B). The flow rate was 1.0 ml/min. and the separation was achieved at ambient temperature. The gradient for the separation of metabolites in all of the matrices was programmed as follows: SolventA:Solvent B; 90:10 changed to 60:40 from 0 to 30 minutes. The column was allowed to equilibrate to 90:10 buffer:acetonitrile for 10 minutes before the next injection.

Metabolite Isolation from Rats (Method C)

The testing dose was prepared by combining a uniform powder of 2-amino-N-[2-(3a(R)-benzyl-2-methyl-3-oxo-2,3,3a,4,6,7-hexahydro-pyrazolo-[4,3-c]pyridin-5-yl)-1-(R)-benzyl-oxymethyl-2-oxo-ethyl]-isobutyramide (tartrate salt; specific activity=5.00 µCi/mg free base equivalent; radiochemical purity 99%), $^{14}$C-radiolabelled as described hereinabove, in a solution of 100% water. The concentration of the dose was 1.5 mg/ml (free base).

For material balance studies, six rats (3/sex) were administered single 15 mg/kg (free base equivalent) oral doses of the radiolabelled test compound by gavage following an overnight fast. The animals were placed in separate metabolism cages and given ad libitum access to food and water throughout the study.

On the day prior to radiolabelled test compound dosing, pre-dose urine and feces were collected from all of the test animals to determine the background count rate in these matrices. Following administration of the radiolabelled test compound, urine and feces were collected quantitatively into pre-weighed sample jars. Urine and feces were collected at 0–24, 24–48, 48–72, 72–96, 96–120, 120–144, and 144–168 hours post-dose.

The total radioactivity in urine was quantified directly in triplicate (0.05–0.50 ml aliquots for each sampling time) by liquid scintillation counting. Samples were combined with Ecolite scintillation cocktail (5 ml) and counted using a Wallac Liquid Scintillation Counter Model #1409. Feces collected at each sampling time were placed directly into tared stomacher bags and hydrated with water before storage at −20° C. Homogenous fecal slurries were prepared using a stomacher. The total weight of the fecal slurries was recorded for each timepoint. Triplicate aliquots (50–100 mg) of each slurry were weighed into oxidizer sample cups and dried overnight before combustion. The samples were oxidized using a Packard Model 307 oxidizer. Liberated $^{14}CO_2$ was trapped, scintillation cocktail was added, and the samples were counted. All samples were counted on the Wallac counter using an internal quench curve and a 2 sigma value of 4 (95% confidence). Counting efficiencies were >95% throughout the sample oxidation analysis.

Pre-dose urine and fecal samples were counted to determine the background count rate for each matrix. The amount of radioactivity in each matrix was expressed as µg-eq/ml and was calculated by using the specific activity of the dose administered. The lower limit of quantitation (LLOQ) was considered to be twice the background rate.

Radiolabelled material in urine and feces was analyzed by reverse phase HPLC. The HPLC system consisted of a gradient pump and a β-radioactivity detector (β-RAM, INUS) equipped with a 500 µl flow cell. Chromatography was carried out on a Zorbax Rx C-18 column (4.6 mm×150 mm; 3 µm) utilizing a binary gradient of a mobile phase consisting of a mixture of 10 mM ammonium formate, 1% formic acid (Solvent A) and acetonitrile (Solvent B). The flow rate was 1.0 ml/min. and the separation was achieved at ambient temperature. The gradient for the separation of metabolites in all of the matrices was programmed as follows: SolventA:Solvent B; 90:10 changed to 30:70 from 0 to 30 minutes. The column was allowed to equilibrate to 90:10 buffer:acetonitrile for 10 minutes before the next injection. Under gradient conditions, the retention time of the unchanged test compound was 13.0 min.

Urine and fecal samples were pooled relative to excreted volume/mass at each timepoint so that >90% of excreted radioactivity was accounted for. Pooled urine was analyzed directly following centrifugation at 3500 rpm for ten minutes to remove precipitated material. Pooled fecal homogenates were extracted with two acetonitrile washings (3 ml/gm), and concentrated overnight under nitrogen stream.

The concentrated fecal extracts were reconstituted in 100 μl of 90:10 10 mM ammonium formate, 1% formic acid/acetonitrile prior to analysis. A radiochromatogram was obtained for each pooled matrix using on-line radioactivity detection β-RAM). Integration of the radioactive peaks provided quantitative assessment of each metabolite as a percentage of total radioactivity in each sample.

Metabolite Isolation from Dogs (Method D)

The testing dose was prepared by combining a uniform powder of 2-amino-N-[2-(3a(R)-benzyl-2-methyl-3-oxo-2, 3,3a,4,6,7-hexahydro-pyrazolo-[4,3-c]pyridin-5-yl)-1-(R)-benzyl-oxymethyl-2-oxo-ethyl]-isobutyramide (tartrate salt; specific activity=5.00 μCi/mg free base equivalent; radiochemical purity >99%)., $^{14}$C-radiolabelled as described hereinabove, with unlabelled compound in a solution of 100% nanopure water. The concentration of the dose was 3.5 mg/ml (free base).

Four beagle dogs (2/sex) were administered single 7 mg/kg (free base equivalent) oral doses of the test compound by oral gavage. The animals were fasted prior to dosing and returned to their normal feeding schedule four hours after dose administration. Animals were returned to metabolism cages which allowed for the separate collection of urine and feces.

On the day prior to dosing, pre-dose urine and feces were collected from all of the animals to determine the background count rate in these matrices. Following administration of the radiolabelled test compound, urine and feces were collected quantitatively into preweighed sample jars and stomacher bags, respectively. Urine and feces were collected at 0–24, 24–48, 48–72, 72–96, 96–120, 120–144, and 144–168 hours post-dose.

The total radioactivity in urine and feces was quantified directly in triplicate (0.05–0.50 ml aliquots for each sampling time) by liquid scintillation counting. Samples were combined with Ecolite scintillation coctail (5 ml) and counted using a Wallac Liquid Scintillation Counter Model # 1409. Feces collected at each sampling time were placed directly into tared stomacher bags and hydrated with water before storage at −20° C. Homogenous fecal slurries were prepared using a stomacher. The total weight of the fecal slurries was recorded for each timepoint. Triplicate aliquots (50–100 mg) of each slurry were weighed into oxidizer sample cups and dried overnight before combustion. The samples were oxidized using a Packard Model 307 oxidizer. Liberated $^{14}CO_2$ was trapped, scintillation cocktail was added, and the samples were counted. All samples were counted on the Wallac counter using an internal quench curve and a 2 sigma value of 4 (95% confidence). Counting efficiencies for $^{14}$C in urine and fecal samples were >95% throughout the sample oxidation analysis.

Pre-dose urine and fecal samples were counted to determine the background count rate for each matrix. The amount of radioactivity in each matrix was expressed as μg-eq/ml and was calculated by using the specific activity of the dose administered. The lower limit of quantitation (LLOQ) was considered to be twice the background rate.

Radiolabelled material in urine and feces was analyzed by reverse phase HPLC. The HPLC system consisted of a gradient pump and a β-radioactivity detector (β-RAM, INUS) equipped with a 500 μl flow cell. Chromatography was carried out on a Zorbax Rx C-18 column (4.6 mm×150 mm; 3μm) utilizing a binary gradient of a mobile phase consisting of a mixture of 10 mM ammonium formate, 1% formic acid (Solvent A) and acetonitrile (Solvent B). The flow rate was 1.0 ml/min. and the separation was achieved at ambient temperature. The gradient for the separation of metabolites in all of the matrices was programmed as follows: SolventA:Solvent B; 90:10 changed to 30:70 from 0 to 30 minutes. The column was allowed to equilibrate for 10 minutes before the next injection.

Urine and fecal samples were pooled relative to excreted volume/mass at each timepoint so that nearly 100% of excreted radioactivity was accounted for. Pooled urine was analyzed directly following centrifugation at 3500 rpm for ten minutes to remove precipitated material. Pooled fecal homogenates were extracted with two acetonitrile washings (3 ml/gm), and concentrated overnight under a nitrogen stream. The concentrated fecal extracts were reconstituted in 100 μl of 90:10 10 mM ammonium formate, 1% formic acid/acetonitrile prior to analysis. A radiochromatogram was obtained for each pooled matrix using on-line radioactivity detection (β-RAM). Integration of the radioactive peaks provided quantitative assessment of each metabolite as a percentage of totalradioactivity in each sample.

Instrumentation

Metabolites in urine and feces were characterized using a SCIEX API 2000 LC/MS/MS mass spectrometer (Foster City, Calif.). Post-column effluent was split and introduced into the atmospheric ionization source via an ion spray interface at a rate of 50 μl/min. The remaining effluent was directed into a β-RAM detector allowing simultaneous detection of radioactivity and total ion chromatogram. The mass spectrometer was operated in the positive ion mode and the ion spray interface was operated at 4500 V. Collision induced dissociation (CID) studies were performed using argon gas at a collision energy of 40 eV and collision gas thickness of ~3.0×10$^4$ molecules/cm$^2$.

Identification of Metabolites

The synthetic standard of the compound 2-amino-N-[2-(3a(R)-benzyl-2-methyl-3-oxo-2,3,3a,4,6,7-hexahydro-pyrazolo-[4,3-c]pyridin-5-yl)-1-(R)-benzyl-oxymethyl-2-oxo-ethyl]-isobutyramide in positive ion mode generated a molecular ion signal at m/z 506 [M+H]$^+$. The collision induced dissociation (CID) product ion of m/z 506 produced major ions at m/z 58, 91, 215, 235, 244, 263, and 421. The product ions at m/z 244 and 263 were rationalized by cleavage of the amide bond connecting the α-methylalanyl-O-benzylserine moiety to the remainder of the molecule. Further loss of a carbonyl group from ions m/z 263 and 244 resulted in the ions at m/z 235 and 215 respectively. The product ion at m/z 58 was the α-methylalanine moiety cleaved α- to the amide bond. The loss of α-methylalanine generated the formation of product ion m/z 421. The product ion at m/z 91 was the tropylium ion from Obenzylserine and benzylpiperidine-pyrazolone moiety.

Metabolite 1 (Method A)

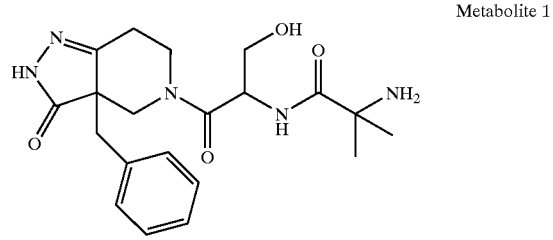

Metabolite 1

([M + H]$^+$ = m/z 402)

Metabolite 1 had a retention time of approximately 7.0 minutes. In a precursor ion scan of m/z 230, a protonated molecular ion at m/z 402 was detected. The CID product ion spectrum of m/z 402 produced major ions at m/z 58, 91, 139, 145, 187, 201, and 230. The product ion m/z 230 was 14 amu less than m/z 244 product ion observed with the unchanged compound and corresponded to N-demethylation at the pyrazolone moiety. The product ion m/z 145 was 90 amu less than the product ion m/z 235 observed with the unchanged compound and corresponded to O-debenzylation of the O-benzylserine moiety. The product ion m/z 58 was consistent with unchanged α-methylalanine. The product ions m/z 201 and 139 were formed by the loss of carbonyl group and benzyl group from the m/z 230 product ion respectively. The product ion m/z 91 was the tropylium ion. The product ion m/z 187 was formed by cleavage of a portion of the piperidine ring containing benzene ring and pyrazolone moiety.

Metabolite 2 (Method A)

Metabolite 2

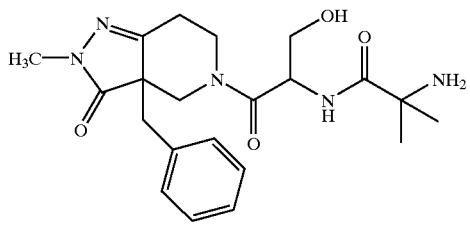

([M + H]$^+$ = m/z 416)

Metabolite 2 had a retention time of approximately 7.0 minutes. In a precursor ion scan of m/z 244, a protonated molecular ion at m/z 416 was detected. This was 90 amu less than the unchanged compound. The CID product ion spectrum of m/z 416 produced major ions at m/z 58, 91, 145, 153, 201, 215, 244, and 331. The product ion m/z 244 suggested no modification to the benzylpiperidine half of the compound, thus isolating the loss of 90 amu from the α-methylalanyl-O-benzylserine side of the molecule. The product ion m/z 58, which was observed in the unchanged compound and corresponded to α-methylalanine, localized the modification to the serine moiety. The product ion m/z 331 was 90 amu less than that of the m/z 421 product ion from the unchanged drug, which was indicative of O-debenzylation of the O-benzylserine moiety. The product ion m/z 201 was believed to have been formed by cleavage of the amide containing α-methylalanine and serine. The product ions m/z 215 and 153 were formed by the loss of carbonyl and benzyl groups from m/z 244, respectively. The product ion m/z 145 corresponded to the α-methylalanyl-O-benzylserine portion of the molecule minus a carbonyl group. This was consistent with the structural assignment of a loss of the benzyl group by O-debenzylation.

Metabolite 3 (Method A)

Metabolite 3

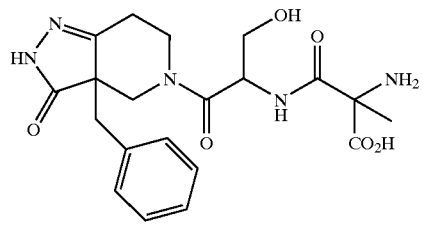

([M + H]$^+$ = m/z 432)

Metabolite 3 had a retention time of approximately 17 minutes. In precursor ion scans of m/z 230, a protonated molecular ion at m/z 432 was detected. A CID product ion spectrum of m/z 432 produced major ions at m/z 91, 201, 230, and 386. The product ions at m/z 201 and 230 were consistent with N-demethylation of the benzylpiperidine moiety. The neutral loss of 46 amu (m/z 432–386=m/z 46), which corresponded to the loss of formic acid, was consistent with the presence of a carboxylic acid at the α-methylalanine moiety.

Metabolite 4 (Method A)

Metabolite 4

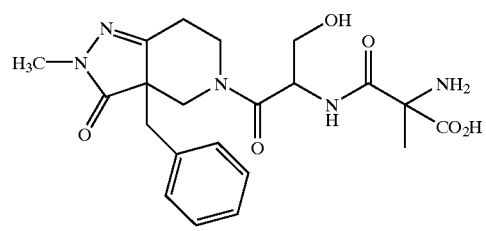

([M + H]$^+$ = m/z 446)

Metabolite 4 had a retention time of approximately 22.0 minutes. In a precursor ion scan of m/z 244, a molecular ion at m/z 446 was detected. The CID product ion spectrum of m/z 446 produced major ions at m/z 129, 153, 215, 244, and 329. The product ion at m/z 244 corresponded to the unchanged benzylpiperidine portion of the compound and the product ions m/z 215 and 153 were the losses of carbonyl and benzyl groups from the ion at m/z 244, respectively. The product ion m/z 239 was the loss of α-methylalanine from the molecular ion, suggesting an O-debenzylated metabolite. This localized the other modifications on the α-methylalanine. Based on the molecular ion, there was an increase of 30 amu on the α-methylalanine, suggesting a carboxylic acid.

Metabolite 5 (Method A)

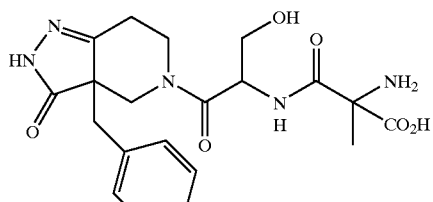

Metabolite 5

$([M + H]^+ = m/z\ 432)$

Metabolite 5 had a retention time of approximately 18.5 minutes. In a precursor ion scan of m/z 230, a protonated molecular ion at m/z 432 was detected. The CID product ion spectrum of m/z 432 produced major ions at m/z 91, 129, 139, 187, 201, and 230. The product ion at m/z 230 suggested N-demethylation of unchanged compound. The product ion at m/z 129 corresponded to the α-methylalanine-serine moiety plus the loss of formic acid, which was also O-debenzylated. This resulted in a 30 amu increase at the α-methylalanine moiety, which was consistent with the formation of a carboxylic acid. This metabolite is similar to Metabolite 3. Since carboxylation at the α-methylalanine resulted in the generation of a new chiral center, Metabolite 3 and Metabolite 5 are diasteriomers.

Metabolite 6 (Method A)

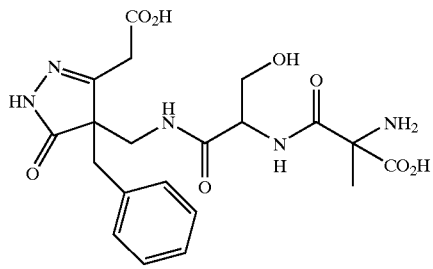

Metabolite 6

$([M + H]^+ = m/z\ 464)$

Metabolite 6 had a retention time of approximately 14.8 minutes. The molecular ion of this metabolite was not observed in the precursor ion scans of m/z 230, 235, or 244. A protonated molecular ion for this metabolite was determined to be at m/z 464. This was confirmed by treatment of the isolated metabolite with diazomethane, thereby forming the corresponding methyl ester derivative having a molecular ion of m/z 478 with a retention time of approximately 23.5 minutes. Similarly, when Metabolite 6 was treated with ethanol/HCl, the corresponding ethyl ester derivative was formed, having a retention time of approximately 26 minutes. The ethyl ester conjugate produced a molecular ion at m/z 492, which was 28 amu higher than the unchanged Metabolite 6.

The CID product ion of m/z 464 produced major ions atm/z 91, 129, 187, and 233. The product ion at m/z 129 suggested carboxylation at the α-methyalanine and O-debenzylation. This left an additional 32 amu to the benzylpiperidine portion of the moiety. The modification of the benzylpiperidine moiety was also suggested by the lack of product ions at m/z 244 and 230, observed in all other metabolites. The addition of 32 amu could be explained by the addition of two hydroxyl groups to this moiety, however, no monohydroxylated metabolite that could lead to a dihydroxylated moiety was observed. Additional evidence for the lack of a simple dihydroxylated moiety was the lack of a product ion corresponding to m/z 276 (m/z 32+m/z 244).

The product ion m/z 233 could have been formed in two ways. It could correspond to the serine-alanine portion plus part of the piperidine ring and also the remainder of the molecule that contains a benzene ring and pyrazolone. The loss of a carboxylic acid from each of these leads to the formation of product ion at m/z 187. The product ion m/z 187 was further fragmented using a higher orifice energy of 120 V. The resultant CID product ions of m/z 187 produced ions at m/z 91, 115, and 127. The presence of m/z 91 product ion, which corresponded to tropylium ion, suggested that m/z 187 contained a benzene ring. This further suggested that the m/z 187 product ion contained pyrazolone and benzene rings and was formed from the N-demethylated metabolite.

Treatment of the isolated fraction of Metabolite 6 with diazomethane produced a product with a retention time of 22.5 min. The CID product ion at m/z 478 produced ions at m/z 91, 187, and 247. The product ion at m/z 247 was 14 amu higher than m/z 233, which suggested methyl ester formation. Similarly, treatment of isolated Metabolite 6 with ethanol/HCl produced an ethyl ester derivative having a molecular ion of m/z 492. The CID product ion produced ions at m/z 187, 203, 261, and 288. The product ion at m/z 261 was 28 amu higher than m/z 233 observed for the metabolite, which suggested the presence of a carboxylic acid. These findings were consistent with the structural assignment shown for Metabolite 6.

Metabolite 7 (Method A)

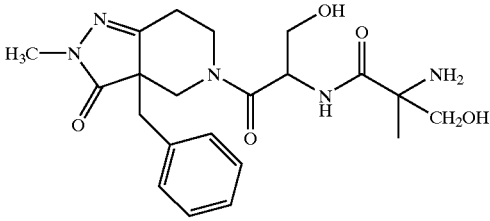

Metabolite 7

$([M + H]^+ = m/z\ 432)$

Metabolite 7 had a retention time of approximately 19.5 minutes. In a precursor ion scan of m/z 244, the protonated molecular ion at m/z 432 was detected. The CID product ion of m/z 432 produced major ions at m/z 91, 115, 153, 215, 244, and 331. The product ion at m/z 244, also observed in unchanged compound, corresponded to the unchanged portion of the benzylpiperidine side of the compound. The product ion at m/z 331 was consistent with the loss of α-methylalanine minus a benzyl group, which suggested that the metabolite was O-debenzylated. The remaining 16 amu indicated hydroxylation at the α-methylalanine. The molecular ion, which was 74 amu less than the unchanged drug, was rationalized as O-debenzylation with a single hydroxylation at the α-methylalanine moiety. The product ion at m/z 115 corresponded to the α-methylalanine-serine moiety cleaved at the α-methylalanine. The product ions at m/z 215 and 244 were due to the losses of carbonyl and benzyl groups respectively.

Metabolites 8 and 9 (Method A)

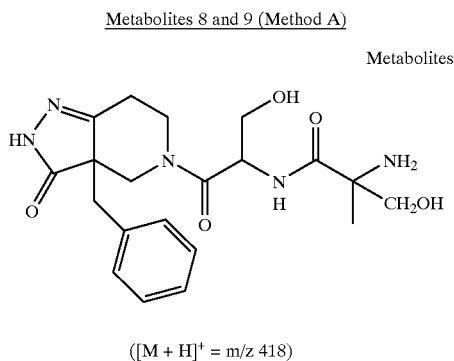

Metabolites 8 and 9

([M + H]⁺ = m/z 418)

Metabolites 8 and 9 had retention times of approximately 15.0 minutes and approximately 15.8 minutes respectively. In a precursor ion scan of m/z 230, a protonated molecular ion of m/z 418 was detected. The CID product ion spectrum of m/z 418 was identical for both compounds and generated major ions at m/z 91, 115, 139, 201, and 230. The product ion m/z 115 corresponded to the serine moiety, which suggested that the metabolite was O-debenzylated. The remaining 16 amu indicated hydroxylation at the α-methylalanine. Given the fact that there were two carboxylated metabolite derivatives at the α-methylalanine, the hydroxylation was believed to have taken place at one of the two methyl groups. Since hydroxylation at this moiety led to a chiral center, there were two possible hydroxylated metabolites. The product ions at m/z 201 and 230 suggested N-demethylation of the benzylpiperidine.

Metabolites 10 and 11 (Method C)

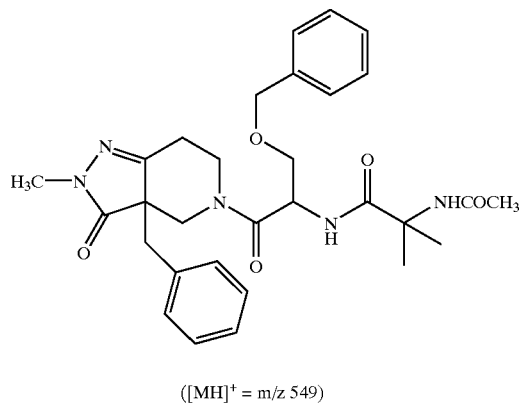

Metabolites 10 and 11

([MH]⁺ = m/z 549)

Metabolites 10 and 11 had retention times of approximately 15.7 minutes and approximately 16.5 minutes respectively. In a precursor ion scan of m/z 244, the molecular ion of m/z 549 was detected for both metabolites. The CID spectra of m/z 549 were identical for both compounds and produced major ions at m/z 91, 176, 244, 261, and 289. The molecular ion was 43 amu higher than the unchanged compound and also had a longer retention time. The product ion at m/z 244 suggested no modification at the benzylpiperidine half of the compound. The product ion m/z 91 suggested no modification of the benzyl group in the O-benzylserine moiety. Based on these findings, acetylation of the primary amine in the α-methylalanine moiety was suggested. The presence of two metabolites was due to isomerization of the chiral centers.

Metabolite 12 (Method C)

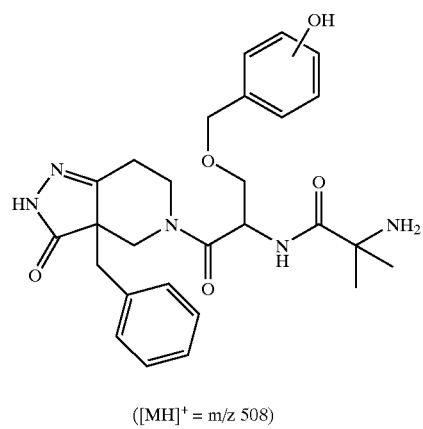

Metabolite 12

([MH]⁺ = m/z 508)

Metabolite 12 had a retention time of approximately 7.9 minutes. In a precursor ion scan of m/z 230, the molecular ion at m/z 508 was detected, which was 12 amu higher than the unchanged drug. The CID spectrum of m/z 508 revealed major ions at m/z 173, 230, and 402. The product ion at m/z 230 suggested N-demethylation of unchanged compound. The product ion at m/z 402 was a loss of 106 amu from the molecular ion, which was due to the loss of a hydroxylated benzyl group. The ion at m/z 173 was due to the loss of the benzylpiperidine portion of the molecule from the ion at m/z 402, and also confirmed the presence of a hydroxylated benzyl moiety.

Metabolite 13 (Method C)

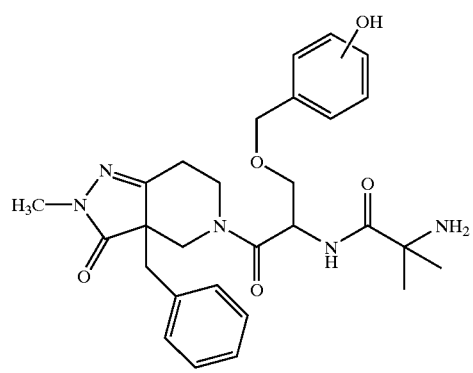

Metabolite 13

([MH]⁺ = m/z 522)

Metabolite 13 had a retention time of approximately 9.9 minutes. In a precursor ion scan of m/z 244, the molecular ion was detected at m/z 522. The molecular ion was consistent with a single hydroxylation of the unchanged compound. A CID spectrum of m/z 522 revealed major ions at m/z 107, 145, 173, 244, 279, 331, and 416. The product ion at m/z 244 suggested no modification of the benzylpiperidine half of the compound. The product ion at m/z 279 was 16 amu higher than the unchanged compound. The site of hydroxylation appeared to be on the benzyl group of the α-methylalanyl-O-benzylserine moiety as suggested by product ions at m/z 107, 173, and 416. The product ions at m/z 416 and 107 represented cleavage of the benzyl group, which was consistent with the loss of hydroxylated benzyl group.

173 isolated the modification to the benzyl group of the O-benzylserine moiety. The tropylium ion at m/z 137 was consistent with two hydroxylations followed by methylation of the resulting catechol derivative by catechol O-methyl transferase.

Metabolite 14 (Method C)

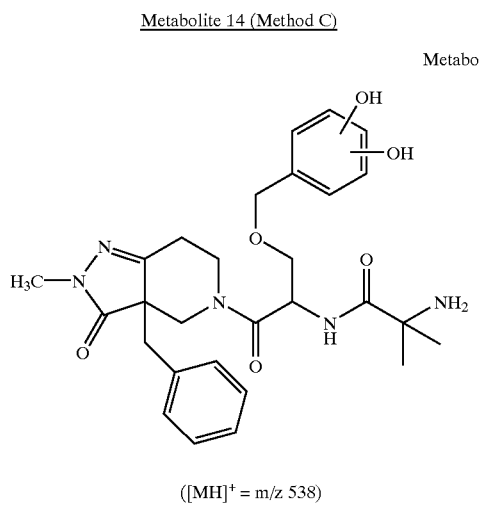

Metabolite 14

$([MH]^+ = m/z\ 538)$

Metabolite 14 had a retention time of approximately 8.5 minutes. In a precursor ion scan of m/z 244, a molecular ion of m/z 538 was detected. The increase of 32 amu to unchanged compound was rationalized by two hydroxylations of the parent compound. The CID spectrum revealed major ions at m/z 123, 173, 244, and 331. The product ions at m/z 244, 331, and 173 isolated the modification to the benzyl group of the O-benzylserine moiety. The tropylium product ion at m/z 123 was consistent with two hydroxylations as well.

Metabolite 16 (Method B)

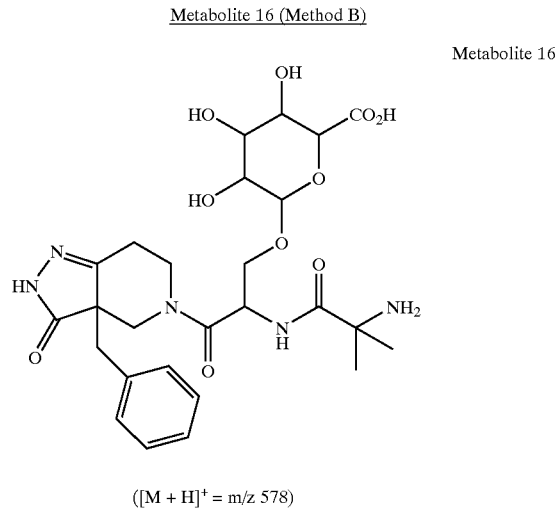

Metabolite 16

$([M + H]^+ = m/z\ 578)$

Metabolite 16 had a retention time of approximately 3.2 minutes. In a precursor ion scan of m/z 230, a protonated molecular ion at m/z 578 was detected. The CID spectrum of m/z 578 revealed major product ions at m/z 58, 145, 173, 201, 218, 230, 317, and 402. The CID spectrum was analogous to that of Metabolite 1, except for the addition of 176 amu to the molecular ion. This was rationalized by phase II glucuronide conjugation. There was a product ion at m/z 218 that was not found in Metabolite 1 and was rationalized as the glucuronide plus $C_2H_3O$. This isolated the site of glucuronidation to the hydroxyl group of serine.

Metabolite 15 (Method C)

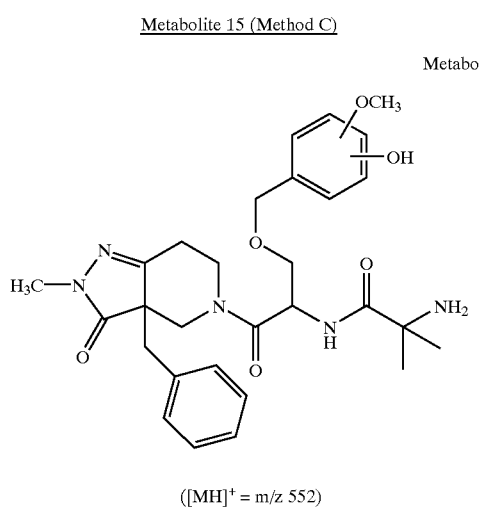

Metabolite 15

$([MH]^+ = m/z\ 552)$

Metabolite 15 had a retention time of approximately 10.2 minutes. In a precursor ion scan of m/z 244, the molecular ion at m/z 552 was detected. The CID spectrum revealed major product ions at m/z 137, 173, 215, 244, and 331. Similar to Metabolite 14, the product ions at m/z 244 and Metabolite 17 (Method B)

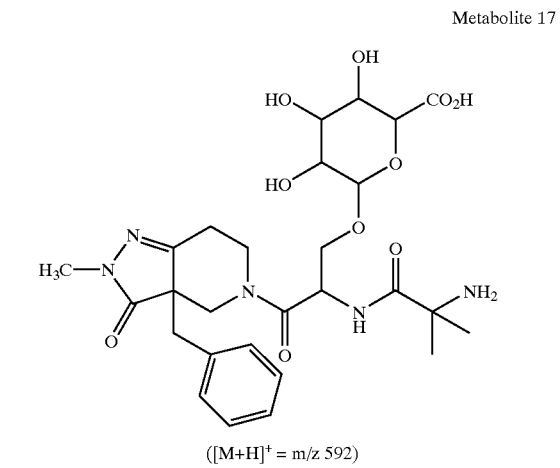

Metabolite 17

$([M+H]^+ = m/z\ 592)$

Metabolite 17 had a retention time of approximately 6.0 minutes. In a precursor ion scan of m/z 244, the molecular ion at m/z 592 was detected. The CID spectrum of m/z 592 showed major fragment ions at m/z 58, 145, 173, 215, 244, 331, and 416. Similar to Metabolite 16, the metabolite had a neutral loss of 176 amu, which suggested a glucuronide conjugate.

Metabolite 18 (Method A)

Metabolite 18

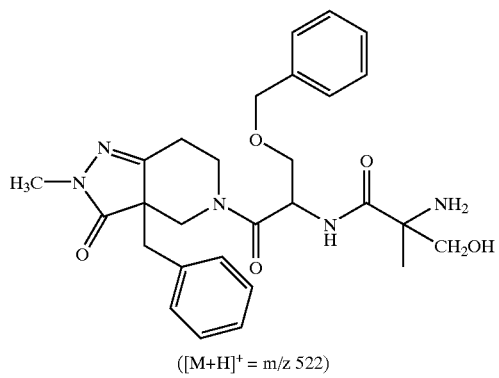

([M+H]⁺ = m/z 522)

Metabolite 18 had a retention time of approximately 23.5 minutes. In a precursor ion scan of m/z 244, the protonated molecular ion at m/z 522 was detected, which suggested monohydroxylation of the unchanged compound. The CID product ion spectrum of m/z 522 produced major ions at m/z 74, 91, 153, 215, and 244. The product ion at m/z 244 suggested no modification to the benzylpiperidine side of the molecule, thus localizing the hydroxylation to the α-methylalanyl-O-benzylserine moiety. The product ion at m/z 74 is 16 amu higher than the ion at m/z 58 from unchanged drug, which corresponded to α-methylalanine.

Pituitary Growth Hormone Secretion Assay

Compounds having the ability to stimulate GH secretion from cultured rat pituitary cells may be identified using the following protocol. This test is also useful for comparison to standards to determine dosage levels.

Cells are isolated from pituitaries of 6-week old male Wistar rats. Following decapitation, the anterior pituitary lobes are removed into cold, sterile Hank's balanced salt solution without calcium or magnesium (HBSS). Tissues are finely minced, then subjected to two cycles of mechanically-assisted enzymatic dispersion using 10 U/mL bacterial protease (EC 3.4.24.4, Sigma P-6141) in HBSS. The tissue-enzyme mixture is stirred in a spinner flask at 30 rpm in a 5% carbon dioxide atmosphere at about 37° C. for about 30 min, with manual trituration after about 15 min and about 30 min using a 10 mL pipet. This mixture is centrifuged at 200×g for about 5 min. Horse serum is added to the supernatant to neutralize excess protease. The pellet is resuspended in fresh protease, stirred for about 30 min more under the previous conditions, and manually triturated, ultimately through a 23-guage needle. Again, horse serum is added, then the cells from both digests are combined, pelleted (200×g for about 15 min), washed, resuspended in culture medium and counted. Cells are plated at $6.0-6.5\times10^4$ cells per $cm^2$ in 48-well Costar dishes and cultured for 3–4 days in Dulbecco's Modified Eagle Medium (D-MEM) supplemented with 4.5 g/L glucose, 10% horse serum, 2.5% fetal bovine serum, 1% non-essential amino acids, 100 U/mL nystatin, and 50 mg/mL gentamycin sulfate before assaying for GH secretion.

Just prior to assay, culture wells are rinsed twice, then equilibrated for about min in release medium (D-MEM buffered with 25 mM Hepes, pH 7.4 and containing 0.5% bovine serum albumin at 37° C.). Test compounds are dissolved in DMSO, then diluted into pre-warmed release medium. Assays are run in quadruplicate. The assay is initiated by adding 0.5 mL of release medium (with vehicle or test compound) to each culture well. Incubation is effected at about 37° C. for about 15 min, then terminated by removal of the culture medium, which is centrifuged at 2000×g for about 15 min to remove cellular material. Rat growth hormone concentrations in the supernatants are determined by a standard radioimmunoassay protocol using a rat growth hormone reference preparation (NIDDK-rGH-RP-2) and rat growth hormone antiserum raised in monkey (NIDDK-anti-rGH-S-5) obtained from Dr. A. Parlow (Harbor-UCLA Medical Center, Torrance, Calif.). Additional rat growth hormone (1.5 U/mg, #G2414, Scripps Labs, San Diego, Calif.) is iodinated to a specific activity of 30 μCi/μg by the chloramine-T method for use as tracer. Immune complexes are obtained by adding goat antiserum to monkey IgG (Organon Teknika, Durham, N.C.) plus polyethylene glycol, MW 10,000–20,000 to a final concentration of 4.3%; recovery is accomplished by centrifugation. This assay has a working range of 0.08–2.5 μg rat growth hormone per tube above basal levels. Active compounds typically stimulate growth hormone release by greater than 1.4 fold.

Assay for Exogenously-Stimulated Growth Hormone Release in the Rat after Intravenous Administration of Test Compounds Twenty-one day old female Sprague-Dawley rats (Charles River Laboratory, Wilmington, Mass.) are allowed to acclimate to local vivarium conditions (24° C., 12 hr light, 12 hr dark cycle) for approximately 1 week before compound testing. All rats are allowed ad libitum access to water and a commercial diet (Agway Country Food, Syracuse, N.Y.). The experiments are conducted in accordance with the NIH Guide for the Care and Use of Experimental Animals.

On the day of the experiment, test compounds are dissolved in vehicle containing 1% ethanol, 1 mM acetic acid, and 0.1% bovine serum albumin in saline. Each compound is tested with n=3. Rats are weighed and anesthetized via intraperitoneal injection of sodium pentobarbital (Nembutol, 50 mg/kg body weight). Fourteen min. after anesthetic administration, a blood sample is taken by nicking the tip of the tail and allowing the blood to drip into a microcentrifuge tube (baseline blood sample, approximately 100 μL). Fifteen minutes after anesthetic administration, test compound is delivered by intravenous injection into the tail vein, with a total injection volume of 1 mL/kg body weight. Additional blood samples are taken from the tail at 5, 10, and 15 min after test compound administration. Blood samples are kept on ice until serum separation by centrifugation (1430×g for 10 min at 10° C.). Serum is stored at –80° C. until serum growth hormone determination by radioimmunoassay as described hereinabove and hereinbelow.

Assessment of Exogenously-Stimulated Growth Hormone Release in the Dog after Oral Administration On the day of the experiment, the test compound is weighed out for the appropriate dose and dissolved in water. Doses are delivered at a volume of 0.5 mL/kg by gavage to 4 dogs for each dosing regimen. Blood samples (2 mL) are collected from the jugular vein by direct vena puncture pre-dose and at 0.08, 0.17, 0.25, 0.5, 0.75, 1, 2, 4, 6, and 8 hrs post-dose using 2 mL vacutainers containing lithium heparin. The prepared plasma is stored at –20° C. until analysis.

Measurement of Canine Growth Hormone

Canine growth hormone concentrations are determined by a standard radioimmunoassay protocol using canine growth hormone (antigen for iodination and reference preparation AFP-1983B) and canine growth hormone antiserum raised in monkey (AFP-21452578) obtained from Dr. A. Parlow (Harbor-UCLA Medical Center, Torrance, Calif.). Tracer is produced by chloramine-T iodination of canine growth hormone to a specific activity of 20–40 $\mu$Ci/$\mu$g. Immune complexes are obtained by adding goat antiserum to monkey IgG (Organon Teknika, Durham, N.C.) plus polyethylene glycol, MW 10,000–20,000 to a final concentration of 4.3%; recovery is accomplished by centrifugation. This assay has a working range of 0.08–2.5 $\mu$g canine GH/tube.

What is claimed is:

1. A purified metabolite of the compound of formula (I)

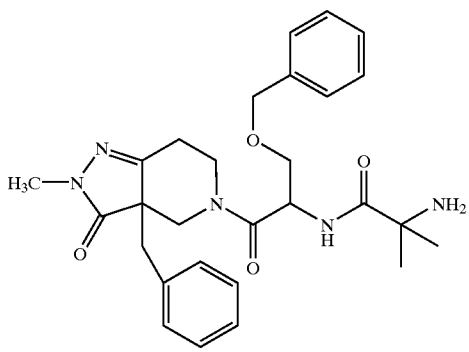

(I)

the racemic-diastereomeric mixtures and optical isomers thereof, the prodrugs thereof, and the pharmaceutically acceptable salts of said metabolites, racemic-diastereomeric mixtures, optical isomers, and prodrugs.

2. A purified metabolite of claim 1 wherein said metabolite of said compound of formula (I) is an acetylated, carboxylated, glucuronidated, or hydroxylated derivative thereof, or a racemic-diastereomeric mixture or optical isomer of said acetylated, carboxylated, glucuronidated, or hydroxylated derivative.

3. A purified metabolite of claim 2 wherein said metabolite of said compound of formula (I) is an acetylated derivative, or a racemic-diastereomeric mixtures or optical isomer thereof.

4. A purified metabolite of claim 3 wherein said acetylated derivative, or said racemic-diastereomeric mixture or optical isomer thereof, is a compound selected from the group consisting of:

(i) a compound which elutes off a Zorbax Rx C-18 4.6×150 mm, 3 $\mu$m particle size column using a flow rate of 1.0 ml/min. and a solvent system using a binary gradient of 90%→30% A, 10%→70% B, [0→30 min.] where A is 10 mM ammonium formate/1% formic acid and B is acetonitrile, at about 15.7 minutes; and has an [MH]$^+$=m/z 549; and (ii) a compound which elutes off a Zorbax Rx C-18 4.6×150 mm, 3 $\mu$m particle size column using a flow rate of 1.0 ml/min. and a solvent system using a binary gradient of 90%→30% A, 10%→70% B, [0→30 min.] where A is 10 mM ammonium formate/1% formic acid and B is acetonitrile, at about 16.5 minutes; and has an [MH]$^+$=m/z 549.

5. A purified metabolite of claim 3 wherein said acetylated derivative is the compound:

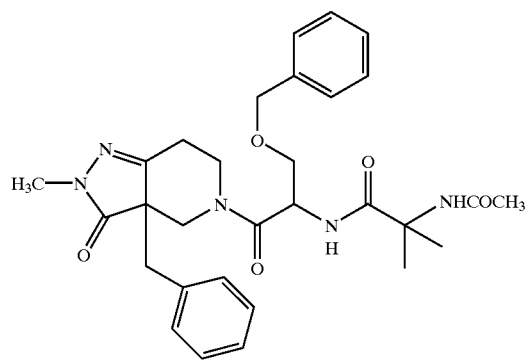

(Ia)

the racemic-diastereomeric mixtures and optical isomers thereof, the prodrugs thereof, and the pharmaceutically acceptable salts of said compound, racemic-diastereomeric mixtures, optical isomers, and prodrugs, wherein said compound has an [MH]$^+$=m/z 549.

6. A purified metabolite of claim 2 wherein said metabolite of said compound of formula (I) is a carboxylated derivative, or a racemic-diastereomeric mixture or optical isomer thereof.

7. A purified metabolite of claim 6 wherein said carboxylated derivative, or said racemic-diastereomeric mixture or optical isomer thereof, is a compound selected from the group consisting of:

(i) a compound which elutes off a Zorbax Rx C-18 4.6×150 mm, 5 $\mu$m particle size column using a flow rate of 1.0 ml/min. and a solvent system using a binary gradient of 90%→60% A, 10%→40% B, [0→30 min.] where A is 10 mM ammonium formate/1% formic acid and B is acetonitrile, at about 14.8 minutes; and has an [M+H]$^+$=m/z 464;

(ii) a compound which elutes off a Zorbax Rx C-18 4.6×150 mm, 5 $\mu$m particle size column using a flow rate of 1.0 ml/min. and a solvent system using a binary gradient of 90%→60% A, 10%→40% B, [0→30 min.] where A is 10 mM ammonium formate/1% formic acid and B is acetonitrile, at about 17 minutes; and has an [M+H]$^+$=m/z 432;

(iii) a compound which elutes off a Zorbax Rx C-18 4.6×150 mm, 5 $\mu$m particle size column using a flow rate of 1.0 ml/min. and a solvent system using a binary gradient of 90%→60% A, 10%→40% B, [0→30 min.] where A is 10 mM ammonium formate/1% formic acid and B is acetonitrile, at about 18.5 minutes; and has an [M+H]$^+$=m/z 432; and (iv) a compound which elutes off a Zorbax Rx C-18 4.6×150 mm, 5 $\mu$m particle size column using a flow rate of 1.0 ml/min. and a solvent system using a binary gradient of 90%→60% A, 10%→40% B, [0→30 min.] where A is 10 mM ammonium formate/1% formic acid and B is acetonitrile, at about 22.0 minutes; and has an [M+H]$^+$=m/z 446.

8. A purified metabolite of claim 6 wherein said carboxylated derivative is a compound selected from the group consisting of:

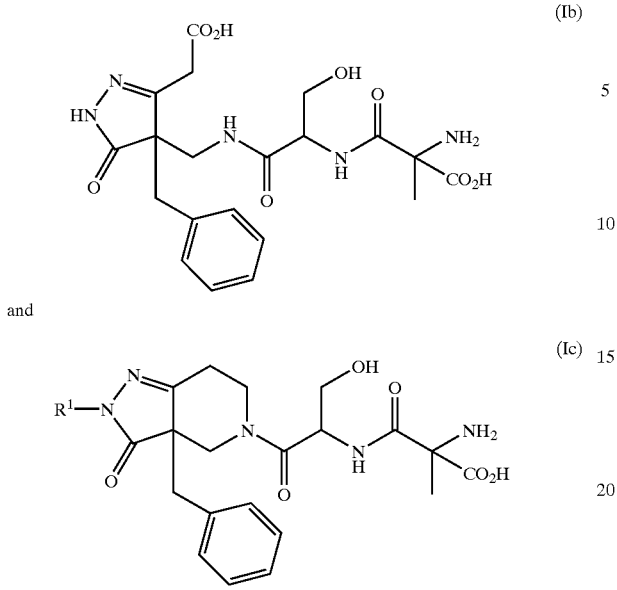

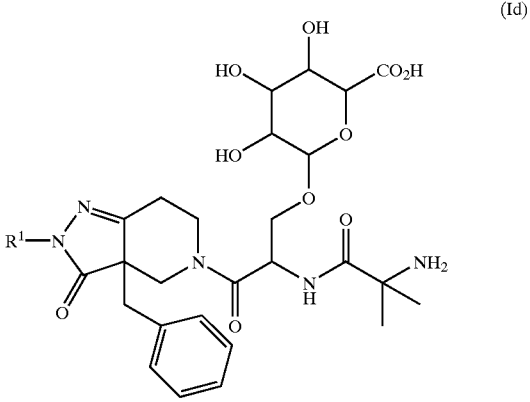

the racemic-diastereomeric mixtures and optical isomers thereof, the prodrugs thereof, and the pharmaceutically acceptable salts of said metabolites, racemic-diastereomeric mixtures, optical isomers, and prodrugs, wherein $R^1$ is hydrogen or methyl, wherein:

(i) compound (Ib) has an $[M+H]^+$=m/z 464;

(ii) when $R^1$ is hydrogen in compound (Ic), said compound has an $[M+H]^+$=m/z 432; and (iii) when $R^1$ is methyl in compound (Ic), said compound has an $[M+H]^+$=m/z 446.

9. A purified metabolite of claim 2 wherein said metabolite of said compound of formula (I) is a glucuronidated derivative, or a racemic-diastereomeric mixture or optical isomer thereof.

10. A purified metabolite of claim 9 wherein said glucuronidated derivative, or said racemic-diastereomeric mixture or optical isomer thereof, is a compound selected from the group consisting of:

(i) a compound which elutes off a Zorbax Rx C-18 4.6×150 mm, 3 μm particle size column using a flow rate of 1.0 ml/min. and a solvent system using a binary gradient of 90%→60% A, 10%→40% B, [0→30 min.] where A is 10 mM ammonium formate/1% formic acid and B is acetonitrile, at about 3.2 minutes; and has an $[M+H]^+$=m/z 578; and (ii) a compound which elutes off a Zorbax Rx C-18 4.6×150 mm, 3 μm particle size-column using a flow rate of 1.0 ml/min. and a solvent system using a binary gradient of 90%→60% A, 10%→40% B, [0→30 min.] where A is 10 mM ammonium formate/1% formic acid and B is acetonitrile, at about 6.0 minutes; and has an $[M+H]^+$=m/z 592.

11. A purified metabolite of claim 9 wherein said glucuronidated derivative is the compound:

the racemic-diastereomeric mixtures and optical isomers thereof, the prodrugs thereof, and the pharmaceutically acceptable salts of said compounds, racemic-diastereomeric mixtures, optical isomers, and prodrugs, wherein $R^1$ is hydrogen or methyl, wherein:

(i) when $R^1$ is hydrogen in compound (Id), said compound has an $[M+H]^+$=m/z 578; and (ii) when $R^1$ is methyl in compound (Id), said compound has an $[M+H]^+$=m/z 592.

12. A purified metabolite of claim 2 wherein said metabolite of said compound of formula (I) is a hydroxylated derivative, or a racemic-diastereomeric mixture or optical isomer thereof.

13. A purified metabolite of claim 12 wherein said hydroxylated derivative, or said racemic-diastereomeric mixture or optical isomer thereof, is a compound selected from the group consisting of:

(i) a compound which elutes off a Zorbax Rx C-18 4.6×150 mm, 5 μm particle size column using a flow rate of 1.0 ml/min. and a solvent system using a binary gradient of 90%→60% A, 10%→40% B, [0→30 min.] where A is 10 mM ammonium formate/1% formic acid and B is acetonitrile, at about 7.0 minutes; and has an $[M+H]^+$=m/z 402;

(ii) a compound which elutes off a Zorbax Rx C-18 4.6×15.0 mm, 5 μm particle size column using a flow rate of 1.0 ml/min. and a solvent system using a binary gradient of 90%→60% A, 10%→40% B, [0→30 min.] where A is 10 mM ammonium formate/1% formic acid and B is acetonitrile, at about 7.0 minutes; and has an $[M+H]^+$=m/z 416;

(iii) a compound which elutes off a Zorbax Rx C-18 4.6×150 mm, 5 μm particle size column using a flow rate of 1.0 ml/min. and a solvent system using a binary gradient of 90%→60% A, 10%→40% B, [0→30 min.] where A is 10 mM ammonium formate/1% formic acid and B is acetonitrile, at about 19.5 minutes; and has an $[M+H]^+$=m/z 432;

(iv) a compound which elutes off a Zorbax Rx C-18 4.6×150 mm, 5 μm particle size column using a flow rate of 1.0 ml/min. and a solvent system using a binary gradient of 90%→60% A, 10%→40% B, [0→30 min.] where A is 10 mM ammonium formate/1% formic acid and B is acetonitrile, at about 15.0 minutes; and has an $[M+H]^+$=m/z 418;

(v) a compound which elutes off a Zorbax Rx C-18 4.6×150 mm, 5 μm particle size column using a flow rate of 1.0 ml/min. and a solvent system using a binary gradient of 90%→60% A, 10%→40% B, [0→30 min.] where A is 10 mM ammonium formate/1% formic acid and B is acetonitrile, at about 15.8 minutes; and has an [M+H]⁺=m/z 418;

(vi) a compound which elutes off a Zorbax Rx C-18 4.6×150 mm, 3 μm particle size column using a flow rate of 1.0 ml/min. and a solvent system using a binary gradient of 90%→30% A, 10%→70% B, [0→30 min.] where A is 10 mM ammonium formate/1% formic acid and B is acetonitrile, at about 8.5 minutes; and has an [MH]⁺=m/z 538;

(vii) a compound which elutes off a Zorbax Rx C-18 4.6×150 mm, 3 μm particle size column using a flow rate of 1.0 ml/min. and a solvent system using a binary gradient of 90%→30% A, 10%→70% B, [0→30 min.] where A is 10 mM ammonium formate/1% formic acid and B is acetonitrile, at about 10.2 minutes; and has an [MH]⁺=m/z 552;

(viii) a compound which elutes off a Zorbax Rx C-18 4.6×150 mm, 3 μm particle size column using a flow rate of 1.0 ml/min. and a solvent system using a binary gradient of 90%→30% A, 10%→70% B, [0→30 min.] where A is 10 mM ammonium formate/1% formic acid and B is acetonitrile, at about 7.9 minutes; and has an [MH]⁺=m/z 508;

(ix) a compound which elutes off a Zorbax Rx C-18 4.6×150 mm, 3 μm particle size column using a flow rate of 1.0 ml/min. and a solvent system-using a binary gradient of 90%×30% A, 10%→70% B, [0→30 min.] where A is 10 mM ammonium formate/1% formic acid and B is acetonitrile, at about 9.9 minutes; and has an [MH]⁺=m/z 522; and (x) a compound which elutes off a Zorbax Rx C-18 4.6×150 mm, 5 μm particle size column using a flow rate of 1.0 ml/min. and a solvent system using a binary gradient of 90%→60% A, 10%→40% B, [0→30 min.] where A is 10 mM ammonium formate/1% formic acid and B is acetonitrile, at about 23.5 minutes; and has an [M+H]⁺=m/z 522.

14. A purified metabolite of claim 12 wherein said hydroxylated derivative is a compound selected from the group consisting of:

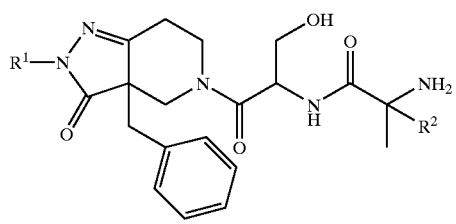
(Ie)

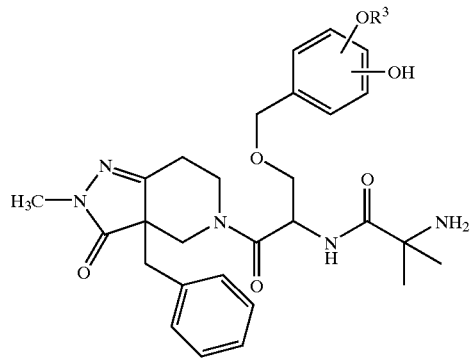
(If)

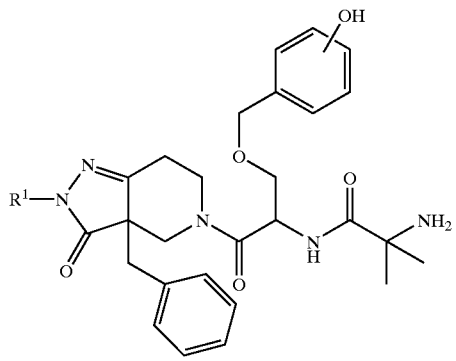
(Ig)

and

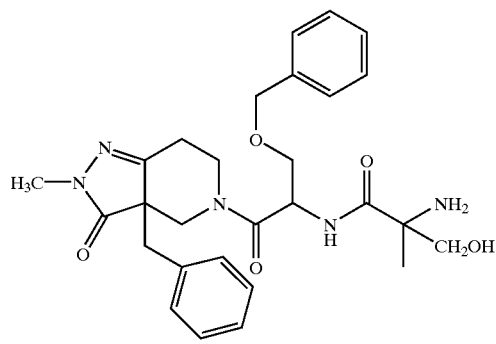
(Ih)

the racemic-diastereomeric mixtures and optical isomers thereof, the prodrugs thereof, and the pharmaceutically acceptable salts of said metabolites, racemic-diastereomeric mixtures, optical isomers, and prodrugs, wherein $R^1$ is hydrogen or methyl, $R^2$ is methyl or $CH_2OH$, and $R^3$ is hydrogen or methyl, wherein:

(i) when $R^1$ is hydrogen and $R^2$ is methyl in compound (Ie) said compound has an [M+H]⁺=m/z 402;
(ii) when $R^1$ and $R^2$ are both methyl in compound (Ie) said compound has an [M+H]⁺=m/z 416;
(iii) when $R^1$ is methyl and $R^2$ is $CH_2OH$ in compound (Ie), said compound has an [M+H]⁺=m/z 432;
(iv) when $R^1$ is hydrogen and $R^2$ is $CH_2OH$ in compound (Ie), said compound has an [M+H]⁺=m/z 418;

(v) when $R^3$ is hydrogen in compound (If), said compound has an $[MH]^+$=m/z 538;

(vi) when $R^3$ is methyl in compound (If), said compound has an $[MH]^+$=m/z 552;

(vii) when $R^1$ is hydrogen in compound (Ig), said compound has an $[MH]^+$=m/z 508;

(viii) when $R^1$ is methyl in compound (Ig), said compound has an $[MH]^+$=m/z 522; and (ix) compound (Ih) has an $[M+H]^+$=m/z 522.

15. A method of increasing levels of endogenous growth hormone in an animal which comprises administering to an animal an effective amount of a metabolite of claim 1, a racemic-diastereomeric mixture or optical isomer thereof, a prodrug thereof, or a pharmaceutically acceptable salt of said metabolite, racemic-diastereomeric mixture, optical isomer, or prodrug.

16. A method of treating or preventing osteoporosis in an animal which comprises administering to an animal an effective amount of a metabolite of claim 1, a racemic-diastereomeric mixture or optical isomer thereof, a prodrug thereof, or a pharmaceutically acceptable salt of said metabolite, racemic-diastereomeric mixture, optical isomer, or prodrug.

17. A method for treating or preventing diseases or conditions in an animal which may be treated or prevented by growth hormone which comprises administering to an animal an amount of a metabolite of claim 1, a racemic-diastereomeric mixture or optical isomer thereof, a prodrug thereof, or a pharmaceutically acceptable salt of said metabolite, racemic-diastereomeric mixture, optical isomer, or prodrug, effective in promoting release of endogenous growth hormone.

18. A method of claim 17 wherein said disease or condition is congestive heart failure, frailty associated with aging, age-related decline in physical performance, or obesity.

19. A method for accelerating bone fracture repair, attenuating post-surgical protein catabolic response, reducing cachexia and protein loss due to chronic illness, accelerating wound healing, or accelerating the recovery of burn patients or patients having undergone major surgery, which comprises administering to an animal in need of such treatment an amount of a metabolite of claim 1, a racemic-diastereomeric mixture or optical isomer thereof, a prodrug thereof, or a pharmaceutically acceptable salt of said metabolite, racemic-diastereomeric mixture, optical isomer, or prodrug, which is effective in promoting release of endogenous growth hormone.

20. A method for improving muscle strength, mobility, maintenance of skin thickness, or metabolic homeostasis in an animal which comprises administering to said animal an amount of a metabolite of claim 1, a racemic-diastereomeric mixture or optical isomer thereof, a prodrug thereof, or a pharmaceutically acceptable salt of said metabolite, racemic-diastereomeric mixture, optical isomer, or prodrug, which is effective in promoting release of endogenous growth hormone.

21. A method for treating or preventing osteoporosis in an animal which comprises administering to said animal a bisphosphonate compound and a metabolite of claim 1, a racemic-diastereomeric mixture or optical isomer thereof, a prodrug thereof, or a pharmaceutically acceptable salt of said metabolite, racemic-diastereomeric mixture, optical isomer, or prodrug.

22. A method of claim 21 wherein said bisphosphonate compound is alendronate.

23. A method for treating or preventing osteoporosis in an animal which comprises administering to said animal a combination of estrogen or conjugated estrogens, and a metabolite of claim 1, a racemic-diastereomeric mixture or optical isomer thereof, a prodrug thereof, or a pharmaceutically acceptable salt of said metabolite, racemic-diastereomeric mixture, optical isomer, or prodrug, and, optionally, progesterone.

24. A pharmaceutical composition comprising a metabolite of claim 1, a racemic-diastereomeric mixture or optical isomer thereof, a prodrug thereof, or a pharmaceutically acceptable salt of said metabolite, racemic-diastereomeric mixture, optical isomer, or prodrug; and a pharmaceutically acceptable carrier, vehicle, or diluent.

25. A composition of claim 24 wherein said metabolite is an acetylated, carboxylated, glucuronidated, or hydroxylated derivative, a racemic-diastereomeric mixture or optical isomer thereof, a prodrug thereof, or a pharmaceutically acceptable salt of said metabolite, racemic-diastereomeric mixture, optical isomer, or prodrug.

26. A method of increasing levels of endogenous growth hormone in an animal which comprises administering to an animal an effective amount of a composition of claim 24.

27. A method of treating or preventing osteoporosis in an animal which comprises administering to an animal an effective amount of a composition of claim 24.

28. A method for treating or preventing diseases or conditions in an animal which may be treated or prevented by growth hormone which comprises administering to an animal an amount of a composition of claim 24 effective in promoting release of endogenous growth hormone.

29. A method of claim 28 wherein said disease or condition is congestive heart failure, frailty associated with aging, age-related decline in physical performance, or obesity.

30. A method for accelerating bone fracture repair, attenuating post-surgical protein catabolic response, reducing cachexia and protein loss due to chronic illness, accelerating wound healing, or accelerating the recovery of burn patients or patients having undergone major surgery, which comprises administering to an animal in need of such treatment an amount of a composition of claim 24 which is effective in promoting release of endogenous growth hormone.

31. A method for improving muscle strength, mobility, maintenance of skin thickness, or metabolic homeostasis in an animal which comprises administering to said animal an amount of a composition of claim 24 which is effective in promoting release of endogenous growth hormone.

32. A method for treating or preventing osteoporosis in an animal which comprises administering to said animal a combination of estrogen or conjugated estrogens and a composition of claim 24 and, optionally, progesterone.

33. A kit comprising a metabolite of claim 1, a racemic-diastereomeric mixture or optical isomer thereof, a prodrug thereof, or a pharmaceutically acceptable salt of the metabolite, racemic-diastereomeric mixture, optical isomer, or prodrug, and a pharmaceutically acceptable carrier, vehicle or diluent in a first unit dosage form; estrogen, conjugated estrogens, progesterone, or a bisphosphonate compound and a pharmaceutically acceptable carrier, vehicle or diluent in a second unit dosage form; and a container.

34. A kit according to claim 33, wherein said bisphosponate compound is alendronate.

* * * * *